United States Patent
Fang et al.

(10) Patent No.: US 12,291,743 B2
(45) Date of Patent: May 6, 2025

(54) METHOD FOR EVALUATING TEA PLANT (+)-CATECHIN CONTENT

(71) Applicant: TEA RESEARCH INSTITUTE, GUANGDONG ACADEMY OF AGRICULTURAL SCIENCES, Guangdong (CN)

(72) Inventors: Kaixing Fang, Guangdong (CN); Hualing Wu, Guangdong (CN); Xiaohui Jiang, Guangdong (CN); Hongjian Li, Guangdong (CN); Qiushuang Wang, Guangdong (CN); Dandan Qin, Guangdong (CN); Chendong Pan, Guangdong (CN); Bo Li, Guangdong (CN)

(73) Assignee: TEA RESEARCH INSTITUTE, GUANGDONG ACADEMY OF AGRICULTURAL SCIENCES, Guangdong (CN)

( * ) Notice: Subject to any disclaimer, the term of this patent is extended or adjusted under 35 U.S.C. 154(b) by 0 days.

(21) Appl. No.: 18/662,886

(22) Filed: May 13, 2024

(65) Prior Publication Data
US 2024/0309433 A1    Sep. 19, 2024

Related U.S. Application Data

(62) Division of application No. 17/254,302, filed as application No. PCT/CN2019/110920 on Oct. 14, 2019, now abandoned.

(30) Foreign Application Priority Data

Sep. 4, 2019 (CN) .................. 201910833662.X
Sep. 4, 2019 (CN) .................. 201910833670.4
Sep. 4, 2019 (CN) .................. 201910833687.X
Sep. 4, 2019 (CN) .................. 201910833698.8
Sep. 4, 2019 (CN) .................. 201910834177.4

(51) Int. Cl.
*C12Q 1/6827* (2018.01)

(52) U.S. Cl.
CPC ..... *C12Q 1/6827* (2013.01); *C12Q 2600/156* (2013.01)

(58) Field of Classification Search
None
See application file for complete search history.

(56) References Cited

FOREIGN PATENT DOCUMENTS

CN    106755308    5/2017

OTHER PUBLICATIONS

Guang-Zhe Lin et al., "Expression and purification of His-tagged flavonol synthase of Camellia sinensis from *Escherichia coli*", Protein Expression and Purification, Issue 55, Jun. 2, 2007, pp. 287-292.

Chinese Association for Science and Technology, "Research progress in tea biochemistry: Research on Secondary Metabolism of Tea Trees," in 2009-2010 Report on Advances in Tea Science, edited by the Chinese Association for Science and Technology, Beijing: China Science and Technology Press, Apr. 30, 2010, with English translation thereof, pp. 1-2.

Yuerong Liang et al., "Section 1 Content and influencing factors of catechin compounds in tea leaves", in Comprehensive use of tea resources, Hangzhou: Zhejiang University Press, Nov. 30, 2013, with English translation thereof, pp. 1-9.

En-Hua Xia et al., "Tea Plant Information Archive: a Comprehensive genomics and bioinformatics platform for tea plant", Plant Biotechnology Journal, vol. 17, Issue 10, Oct. 2019, pp. 1938-1953.

*Primary Examiner* — Amanda Haney
(74) *Attorney, Agent, or Firm* — JCIP GLOBAL INC.

(57) ABSTRACT

A molecular marker combination linked to quantitative traits of tea plant (+)-catechin content, including a SNP site 1, a SNP site 2, a SNP site 3, a SNP site 4, a SNP site 5, a SNP site 6, a SNP site 7 and a SNP site 8, which are located in tea genomes Scaffold4239:309117, Scaffold3614: 66549, Scaffold349: 3413816, Scaffold1989: 2316385, Scaffold451: 940283, Scaffold3727:442660, Scaffold115: 803980 and Scaffold920:281727, respectively, and genotypes thereof are extremely significantly correlated with the (+)-catechin content is provided. A detection method for detecting each site, and one or more molecular marker site is used to evaluate the tea plant (+)-catechin content.

1 Claim, 24 Drawing Sheets

Specification includes a Sequence Listing.

Scaffold4239:309117 (as shown in SEQ ID NO:1)

GAAGGCTCTGGAGTAGCTGAAGTTGTTATGAGCTTGTCTAGGCCGAAATCA
GCGAGGTGAGCTTCAAAATCGGCGTCGAATAGGACGTTCTGAGGCTTGAC
ATCGCCATGAACCATGGCGGTGGAGTGGAGGAAGGCGAGGCCGCGGGCGA
TTCCGAGGGCTATTAGGTGGCGCATTGGCCAATTCAATACATGCCCGTCTTG
GTGAGAAGCTTCTTGAAGCAATGTGGCTAGGTTTCCGTTAGGCATATAGTC
GTAGACTAAGAGTCTGAGGTCTGGTGGTCCGGCGAAGTACCCACGGAGGA
CTGTGAGGTTTCTGTGCTTCACTCTCCCGAGCGATTCGGCTTCTTTTCTGAA
CATGTTTTCGTCTAGCGATCCATCAGGGAGTCTCCGAATCGAAAGCACCATT
CCATCACTGTAACAGGCTTT<u>GAAGACTAACCCGTATCGAG</u>TCCTGCTTAG     upstream primer
AACGTTCTCTTCATCGAATTGTCTCGTTGCTTCGGTTGTTTCNGCTAGAGTG     (as shown in SEQ ID NO:2)
ATCTTGTTATTGAACATAACAAGCTTTGGACCGCCATTATCGCCACTTCCAC
GACCTCCGCTGGCTGCAGCTGAGCTTGCTCTTGCTGGGCTGCGCTTTTTCT
CTCCGGCAGCCTTTTCTTTGAGCCTCTTGCGCCA<u>CCGCAAGAGACTGTAA</u>   downstream primer
<u>GTGT</u>AGAAGCAACAACACAGTGCTAAGAGGAAACCACCACTAACAGCCA   (as shown in SEQ ID NO:25)
TGGCAATAAACATGATCAGCCTCTTCTTCCTATTACTCATCTCTTCGCATTTC
GTGCTTAAGGGTTTCCCACATAAGTTCGGATTTCCTGCATAATCAGATGGAT
CGTTGAATCTTGAAGCCAGCATTGTTGGAATCTCGCCGGAGAGGTTGTTTT
GGGATACATTGAAGTAGACCAAGCTAGAGATGAGTGAAATGTTTGCTGGAA
TCGGTCCGGTCAGGTTGTTTGCAGAGAGATTGAGGACTGTGAGGTTTGATA
AATTGGACAATGAGTCTGGTATTTGGCCTGG

FIG. 2

Scaffold3614: 66549 (as shown in SEQ ID NO:4)

GAGTCATGGGTTTCTTAAATTTCTCTAAAAAATATTTAGGTGGTGACTCTGT
ATCTGGCAAAATAGTCCATTTTTTGGCAATTTGATTCAAAATCAGTTTTCCAA
CATATTTGCCGAATTGGGACTTTTTTGGTGATTATCTATTTCACATTGCACATG
TGAAATCAGATTCAGAACCGTGGGAGTCCGATACTGTAGGGCTTATTCGTC
TTCCGAAAAGGGGCATGCAAAGTCGAACTACAAGTCCCCTGGGGAGGATG
GATTGCAAAATTACCGTACACAGTAGCAATCCCGTCTTTAAAGGCGTACTTT
ACCAACTGATGGACCATT<u>GATGACACAACCCTCATCTG</u>ATGTAGCCAGGG        upstream primer
TCTTCCCAGTAGTAGATTGAAAGTGTCCGAAACATCCATGACATAGAATTTA         (as shown in SEQ ID NO:5)
ACCTGATGCTCAGACGGGCCGAGTAGGATATGGCTCTTAAACATTACCATG
ACATCTTGGCTCGTATTGTCATATAAGCCTAAACGGCNTGGGTCGTGGGCGT
AAAGTTAGTCGGCCTCACACCGATGGCATAGGCG<u>GTCCTTACCGGGCATA</u>        downstream primer
<u>CATT</u>AATCGCCGATCCGTTATCTACCAACACCACTGGAATCCACTTTTTCTG         (as shown in SEQ ID NO:26)
ACTTTCCAGCGTTACATATAAGGGCCAATTGTGGTTAGCACCCTCAGGTGGT
AACTCTTTATCTATAAAGATATCACTGGCGTAACATCCCCGGATGTAACCA
ATGATACCAATTGGTCAGCAGTGGTTTCGATAGGGAGTTTGGTCCGGTTCAT
TGCCTCTAGCAGCAGTGCCTGTCTATGCTCCCGAGATGCCATGATTAGCCCC
CAGATTGATATGTCGGCCTGAATCTTCTTAAGCTGTTTCAAGACCAGGTTTT
CTTCAACATCCTTCTCTTTTGATTTCTCGACCCCCACTGTCCTTGATATATGC
CATCTTTTAGGGTTATCACCCATTGGTACCCCTTTCGGTCTAGATTACCCTGA
CTTTAAGGTCTCCTTCTC

FIG. 3

Scaffold349: 3413816 (as shown in SEQ ID NO:7)

ATAATCTTTTTGTACTTGTTCAGGTGGAATGAAGCAATCAACCGAGAGTCC
AGGAACATTGAATGCTAGGTCGTCGATCTTCCAAGTCTCCTCCATCCGTGT
GATTGCTGTGCCCGCTCTCAGATTGTCCCCAAATCTTGAGATGATCACACT
TGATTGGCCAGAATGCGCGATCATCGTGCCCTCCACCATCCGATAGTCCTC
GATTTTCGTGCCCATGGTGGTCTCCCAATAGGTAGGGTAGGTTCCGGGGG
ACTGGATTCTGGTGAGGTAAGAGTCCTCTAAATACACTAGCAGACCACTT
CTTTGGCTGAAGTAACCAAACATGACATGCTTGATCA<u>TCTCTGCACTGTT</u>  upstream primer
<u>GTCACTC</u>CGATCGGCTAGGTCCGTCTGATCCGCGGACAATTTCAACACGA    (as shown in SEQ ID NO:8)
AGCAATCGACGCTCAAGATTCGTTTTTCGCCCACGTATTGTGCTAGGGAAA
ACACAGCCGATACAGCCACAGGATCTAGTCCCTGCATAAATAACANTATG
TTTTTTACATAGAGGAAAATAATATCTGTCACATGAATTCTACTCCATTTT
TTAA<u>CCTTCTAAGAAGTGTGGTG</u>AAAAAAATATTAAATCCATTGGGTA     downstream primer
AAATATAACAGTCTTTAACATAACAATATGGCGAACTATACATTCAATTCT    (as shown in SEQ ID NO:27)
AGAAAATGTCTCATTTTTATAGATTTTTATGAAAGGGATCAACCTTCTTTT
TTTTTATTGGAAGCACTATATAAATAATGTCAAATAGTTTTCCAAACTTAT
CTAAATAAAGTTTTAATAATTTTAATCCACACATTTTGAATTTAATTTACTT
ATTTTTAGTAGATAACATTACCACAGTCAAAAAGAGTGCCAACATGAACC
TCCAGCACACTTGAAGAGCACTTGACGATCATATTGGGAAAGTTACCAGC
CAGCACTCCCAAAAAAAAAAAAGAAAAAAAGATAAAAGATTAAAAAAA
TTAGTAAAAAGTGACTTTACAAAAGGAATATTCCACCTCTG

FIG. 4

Scaffold1989: 2316385 (as shown in SEQ ID NO:10)

AATTAATAAAGACTTGAACAGTGAGGAGGACAATGGAGAGAGGGATTTCA
TGGAGGAGTTTCAGAGAATTAGCTTATTTGATGAGTTGTTTATTTTATTTTAT
TTTATTTTTACTTACAGTGGTAGATGCATCCCATCCCCATCATCGTCCCAATC
GTTATTGCCATGATTTTCATGTTTCATCAGGTGTTGCTTCTCTTGTTTGTGCT
TCCAACTTTCCATCCTCTCTTTCCAAGCTACGCTGCCATAGCCATAAGCAGC
CAAATCCTTGGAAGGATCCATGGATCGAGATTGCACTGCAAAAATGGGCAG
GGGATTATCATACAGATTTGACCTTCAACGTGGGAGGGAGGGGAGATAA    upstream primer
AAGGAAACCATAGCGTAGCGTAGCATAGCATAGGAAAGCAAAGCAGAATT    (as shown in SEQ ID NO:11)
AATTAAAATTACCGGGTAGGCTAGGATCTGAGAAAGGAAGTGGATGAATCC
TTCTGCTGCTGCTGCTGCCACCACCAACACCCACTNTCGATGGAACCA
ATGCATGTTGTTCAGGAGGAATATCATCATCCACCTGCAAACACAAACGCT    downstream primer
GCAGGTCTCAGGCTCCTGCTGTCTGAAATTTGCATACAATGATTTTTAGAAT    (as shown in SEQ ID NO:28)
TCCACAGCAACAGCAACAGCAACAGCAACGGTAGTCGTACCATATGGCCG
TTGGTAAGGAGGGGAAGTTGAGGCAAAGTATTACTATTATTAGTATTGTGAA
AGACATGTGGGTGCAATTCGGATGAGTCGAAAATATGGCCATAGCTCATGT
GCGAACCACCGTGACCGTGAAGTATAGCCTCTGAACGAGCAAGAGAGTGC
TGCTGTGAATCCAGTAGTTTAGCACTGTCACGAACCCTCCCTTCAAAATTG
AACTCGTTTTCCACATCGTCAATGTCATCTTCTTCTTCATCACCCTCCACTCT
AGCACACCCTGCATCATTCATCCATCCATTGATCATCCGGGTAGAACTAACA
AATTTTAACAAATATCGAATCCCCCC

FIG. 5

Scaffold451: 940283 (as shown in SEQ ID NO:13)

CGGCGGGCTGTTCCAAGAAAAAATATAAAATTAAATAAGTTTGTATATTG
TCCTGCCGGGAAACAAATGTGGAATCATTACAAAGAATTAAGAGAAGCAC
TTACATTGCTCCATCTTTTATCGAGAAATTCATTGATCGCAATGGCGTTTT
GTCCGTACATCATAGGAGTCGGAAGAGTGAGAGAGCCATCTGATGCACAC
TAAAGAAGGACAGAAACTGTTTGAGGAACCTGAACATTTTGAGGATAAGT
CAAAAAAAGTTAATTAGGTTTCGGAGTCCAGTGATTGTCGAACCAACAAA
ACAAAACTTATATGCTGTAAAAGAACTTCAACTTACCTA<u>GTAATAGACGG</u>  upstream primer
<u>TGCAAACCC</u>AATTGTATAGTAGGTAAGTACGATCCATATCACAGATTCCA  (as shown in SEQ ID NO:14)
TGAATGAAACGGGAATTCGGAGGAGCCAAATTGGCAAGCTAAAAGCCCA
TGCAGGGAAAAACAAGCTATCCCTCTGTTTAAAGAACACGGGAAGCTTAC
NAACCGTCATTGCAAGCTCTGCCATCCCATTGAACATTATATTAACAAGAC
TGAAAAA<u>CAGCGCTCCCAAATACTTTG</u>AAGCATCTTCTACTGTTCCGGTT  downstream primer
TTCATTTCTGTTCTTAAAAAAACAGTGAGGGCAATTGTGGCCATGATTGTT  (as shown in SEQ ID NO:29)
ATCTGAGTGGTTTTGAATATGTATGTGAAAGAGTTGCGCTTCATTAGCAGC
CACTCCCTCGATAAGCATGCCTTGAAGAGTTCCCGATTGGAGATGCCATA
ACTCTCAGTCACCAACGCAGCAGGGTGGGCTTTGGACTGGTCATAAGGAA
TTCTAAGTTCTTCAGTCATCTGTTGCCCGATGTGGAAAGAGTTGAAGGCCT
GTGCAAAGTCGTTCACCGAGACATATCTGTAAGGTTGGTTCTTTTTGAACC
AATACTGTTCTTGGTCCTTCTTGGAAGTTACTTCTTGGAGAAAATCTGCAA
CTCCTTTCCTTTTGGGGCATTTGAATCCCATATATTCAAAGAACT

FIG. 6

Scaffold3727:442660 (as shown in SEQ ID NO:16)

CCCTACACTTTTTTTTAAATGGTGAGTTGTCCCCACACTTCAATATCGCAC
ATAATACACGTTTTCATTTCATGTCGTCTTCAATACAGAAGACTCGCACCAC
TATTAGCTAGCCTATTATAGCCCCTCCTCTTAACTACCTCTACCCCCAATTCC
TCTCTCTCTCTCTCTCTCTCTCTCTCTCTCTCTCTCTCTATAAAATCAAAAAT
AAGGACTTGTTTGTTTCATCGTACTTTGTTTTATAGGATCAACCTTGGAAGC
CACACCTAGGCATGAGTTGCTCAATAGATTGGCCAGAACCAA<u>TTGTCCGT</u>    upstream primer
<u>GTCCAATCCTTG</u>TCCGACAGCGGCACCCCCACCATCCCCGACTGCTACGT   (as shown in SEQ ID NO:17)
CAAACCGCCACAGGACCGGCCGGTAGTCAACTCCTCCTCCAACCACCATG
ACACCGATGTAAACATCCCCTTAATTGACCTCGGAGTTTTAACATCCGGGG
ACGACAATACTACTCTAAGAGCAACCACCATAGCCCANATATCCGAAGCGT
GTCGTGAGTGGG<u>GCTTCTTCCAGGTGGTCAAT</u>CACGGAGTGAGCCCCCA   downstream primer
CTTGATGGATCGCGCCAGGGATATCTGGCGCGATTTCTTCCATCTTCCAATG   (as shown in SEQ ID NO:30)
GAAGAAAAGCAAGTTTATGCGAATTCACCCAAAACGTACGAAGGGTATGG
AAGTCGGTTAGGCGTCCAGAAAGGTGCCATTCTCGACTGGAGCGACTACTA
CTTCTTGCACTTTCTTCCGTGCTCGCTTAAAGATCATAACAAGTGGCCCGCC
TTGCCAGCTCCTCTCAGGTGAATTGCTTTAATTTTTAATTTTTTAATGTAATA
ATAATATATAAATGTTGGTGACTTGTATACTTTAATGTAACAACCACCATCTAT
TTGGACTTTACTGATCTAATTTTATGTATTACTATATTACTGGTTGTGTTTAGG
GAAGTGATAGATGAGTACGCGGACCACTTAGTAAAGCTAAGTGGGCGATTA
ATGAAGGTTTTGTCAATAAAT

FIG. 7

Scaffold115: 803980 (as shown in SEQ ID NO:19)

AATCATTAAGAGTCATTATGGTAATCATGAGCTTAATTACTCCAAGTAAAGC
CAATCTTCATCATAGAAATAAAAATTACAAAAAAAAAAAAAAAAAAAAAAG
TCTTTCAGCTGAACAACCCATCCCTGCAACTGCACCACCATAATTGAGATCT
AAATCTGAAGGAACTTGCTTGAGATCTAAATCTGAAGGAACTTGCTTGCTT
AGGAACATCCACATCCATGATTTCTACAATTTTTGGAAGACACAGAACCAG
AGAAGATGACTCAAAATCAAGCAGCAATTGTAAGAAAATTCGACCAATCG
AAATCATCTTGGAATTAATCATTGTAGCCTC<u>CTTCATCTCCACCACACTTC</u>  upstream primer
TCCTCCTACTTCCATGCGATTACGTCGACGGCAGCCCTATTCCCACCATCATA  (as shown in SEQ ID NO:20)
TTCAAAGGACTCCCCTCCACCTTCCACGCCTTCGTCGTCTCCCTCATCTTCG
CCTTCTCCGGAGCCTTGAGCGCCTTGTTGATCCACGACNCATCCCTCTTTGC
CAAGCTCTGCGAGTTCTCTTCCATGGCCTCCATGACCTCTGCT<u>CTCTCGTT</u>  downstream primer
<u>GCTACTTTGGGC</u>TATGTTCTTCACCTGTTTTCAACCACAACCCAGGTAAAA  (as shown in SEQ ID NO:31)
CTCGAATTCAGACATCACATGGTAAGAAAACAAGTTATTAAGGTTTTTAACC
TTATAAAGACTTTTTTTCTTTTTTTCTTTTCCTTCCTGTCCAACGGACACGTGG
TGTGTTTTAAAATTAATAAATCGTGTATCAGATATGGATATACAATCGCGTGG
TCAGTTGAAATTACTATTGGTATGCTTTATATACCGTGTCGTGTGTAAAATTA
AAACTTGTTTTGTGATGTTGTTGGTCTGTTATGTACTTGGTGTTGTTGAAAT
AATATTACCATAAATTTGAATAAGCCTTTATTATGTGGAGATCCGATGGATTA
ATGATGCATATTGTCACAGAATTCAAAATGATTTCATTTTGAGCATGGTGAC
GAGGGTTCCAAGCCCTG

FIG. 8

Scaffold920: 281727 (as shown in SEQ ID NO:22)

AGGGAGACTTTTATCTTGAGAGCTAGAAGAAGAGAAAGTTAGAGAAAAGA
AAGAGAAGTAGGAAGAAAAATCAAAGGGAATTCACATTCGTCCTTTTGGAG
TTGAGAATTGAACACTTAGGTGATTTCGAAAATCATAAATGAGGTGTGTTA
AACTAATATCGTTCAGCTACAGTTACTCAGTAAATTCTCTTTCTCAGAGGCT
ACGCAGGTGTAGTTTGAGTTAAACTTGGCCACTTAAACTAATGGAACCATT
AGGGGCCCAAGCTAATTAGTTCCTAGAACAAAGGAGAGAGGACGGAGAA
GCATAGAGAAAGTTAGAGAGAAACTTTTTTCTTGAGAGATAGAAGAGATAG
TTAGAGAAAAGAAAGAGAAACGGGAAAAAAATCATTGGGAA<u>TTCGCATT
CGTCCTTTTGGG</u>CTTGAGAATTGAACAGTTGGGGAATTTGGGAAACCTTA    upstream primer
                                                     (as shown in SEQ ID NO:23)
AATGCGGTGCTTATGTTTAACTAATATCGTTAAGTGCCAATTACTCAATAAAT
CCTCTTTCTTAGATGCTAAGCAAGATTTAGTGTAGTTAAACTTGGCCACTTA
AGCTAATGGAACAGTTAGGGTCCCAAGCGAATTAGTTTCCTAGAACAAAAG
ATAGAA<u>GGATGGAGAATGTAGCACGT</u>TCGTGAGGGACCCCGCTACTACA    downstream primer
GTTCGGACTCGATTTGTGTCACGGTTCTTAATCTGAACCAAAGAGTCCAAA   (as shown in SEQ ID NO:32)
TCCGGCAAATCGTTTTGAGAAACAGATTTTTTTGAAAAGAAGTGCCAAACAT
GGACTGCTTTGCTAGATATAGAGTCGCCACCTAAATATTTTTTTAAAATGGG
GAAATTTAGGAAACCCTAACTTGGTGCCAAAGGCCACGTGTCCGTCATTGC
CAAAGTTGCCTGGGCTCGGGAGCTTGGGTACGATTGGGGAAGGTCAGCTAT
GAGCACCCCTCTCGCCCGATCCGAAGATCGGCCTCTACTAACCGTGATATC
CGTTTTTGAAAACGTTATGTGTTCTTAAACCAATT

FIG. 9

SEQ ID NO:41: TCACTCTAGCTGAAACAACCG

SEQ ID NO:42: AACACCCACTGTCGATGGAAC

SEQ ID NO:43: ATAAATAACAATATGTTTTTT
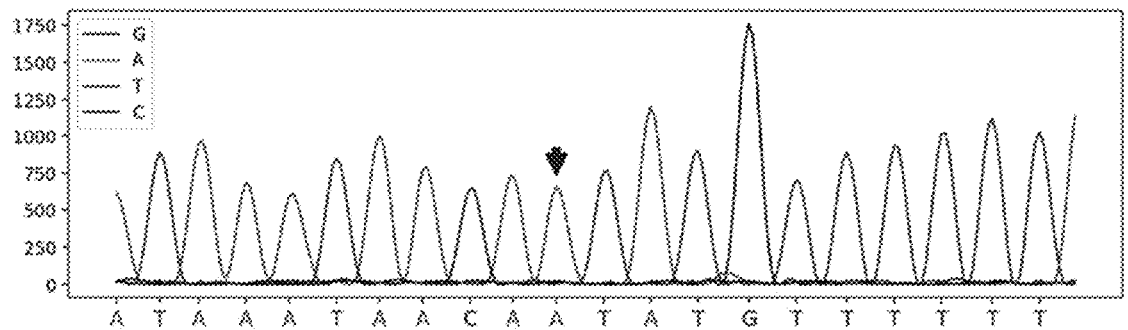
FIG. 36
SEQ ID NO:44: GATCCACGACACATCCCTCTT
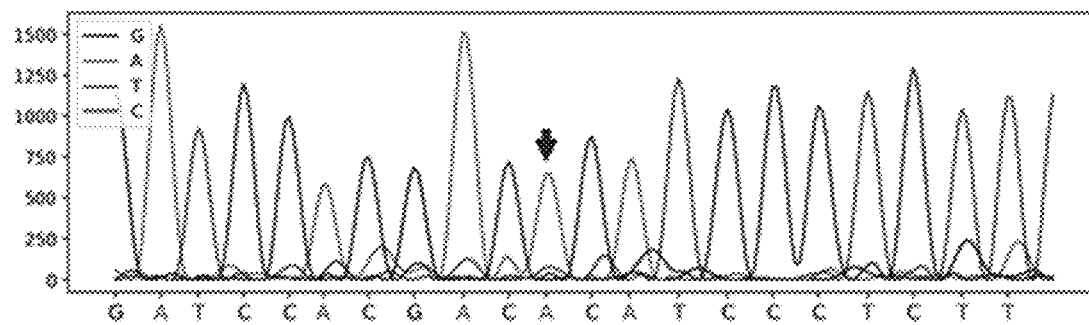
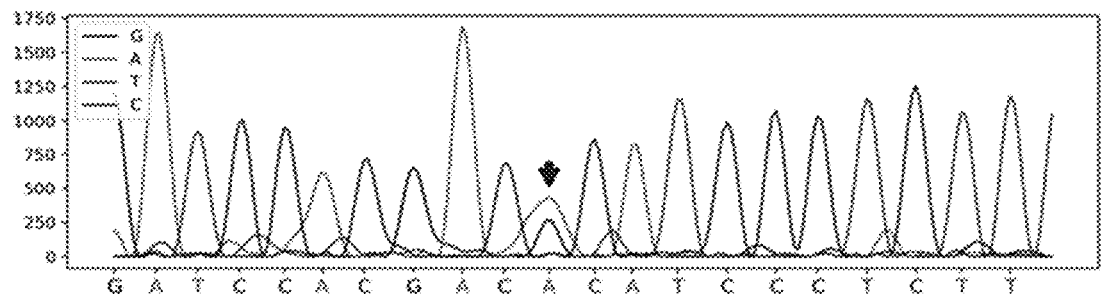
FIG. 37

METHOD FOR EVALUATING TEA PLANT (+)-CATECHIN CONTENT

CROSS-REFERENCE TO RELATED APPLICATION

This application is a divisional application of and claims the priority benefit of U.S. application Ser. No. 17/254,302, filed on Dec. 21, 2020, now pending. The prior U.S. application Ser. No. 17/254,302 is a 371 of international application of PCT application serial no. PCT/CN2019/110920, filed on Oct. 14, 2019, which claims the priority benefit of China application no. 201910833687.X, China application no. 201910834177.4, China application no. 201910833698.8, China application no. 201910833662.X, and China application no. 201910833670.4, filed on Sep. 4, 2019. The entirety of each of the above mentioned patent applications is hereby incorporated by reference herein and made a part of this specification.

REFERENCE TO A SEQUENCE LISTING

The instant application contains a Sequencing Listing which has been submitted electronically in XML file and is hereby incorporated by reference in its entirety. Said XML copy, created on Mar. 27, 2024, is named 102274-us-sequence_listing and is 29,861 bytes in size.

TECHNICAL FIELD

The present invention relates to the technical field of molecular genetics and breeding, and more specifically, to a molecular marker combination linked to quantitative traits of tea plant (+)-catechin content.

BACKGROUND

Tea (*Camellia sinensis* (L.) O. Kuntze) belongs to the genus *Camellia* (Theaceae), which originated in southwest China, with a cultivation history of more than 5,000 years. Tea, coffee, and cocoa are collectively referred to as the world's three major non-alcoholic beverages, which have important economic value and have an important impact on society and culture.

(+)-Catechin (C) is an important secondary metabolite in tea plant that affects flavor. It not only affects tea quality, but also has a variety of physiological functions. Studies have shown that (+)-catechin is an important health component of tea and has multiple functions such as preventing and treating cardiovascular disease and preventing cancer. It is a reducing polyphenolic substance that is easily oxidized by air in aqueous solutions and is often used as an antioxidant. Studies have shown that (+)-catechin (C) can inhibit the proliferation and migration of human liver cancer cells (HepG2) and induce apoptosis of the of human liver cancer cells. Dextro-catechin ((+)-catechin) also has various effects such as reducing capillary permeability, anti-diarrhea, hemostatic, anti-virus, fungicidal, inhibiting angiotensin converting enzyme (ACE) and preventing gastric ulcers. (+)-Catechin (C) has protective effects on dyslipidemia caused by iron overload. (+)-Catechin (C) can improve learning and memory disorder in mice caused by aluminum overload, and has strong antioxidant capacity.

Based on the importance of (+)-catechin to tea quality and physiological functions, it is of great significance to breed tea plant resources with specific (+)-catechin content. At present, tea plant breeding is mainly carried out by conventional methods, and excellent individual plants are selected from wild populations and hybrid offspring for systematic breeding. This method is time-consuming and inefficient, which makes the replacement of new varieties slow, and it cannot quickly meet the public's demand for new products. Since molecular marker-assisted breeding can select breeding materials at the seedling stage, it can significantly improve breeding efficiency.

The discovery of molecular markers closely linked to the excellent traits of the tea plant is the basis for the development of molecular marker-assisted selection breeding for the tea plant. However, due to the limitation of the research progress of traditional quantitative trait locus (QTL) mapping, it has not been able to find a SNP molecular marker site that affects the (+)-catechin content.

SUMMARY OF THE INVENTION

Objectives of the present invention are to overcome the shortcomings of the prior art and provide a molecular marker combination linked to quantitative traits of tea plant (+)-catechin content.

The first objective of the present invention is to provide a molecular marker combination linked to quantitative traits of tea plant (+)-catechin content. The molecular marker combination comprises a SNP site 1, a SNP site 2, a SNP site 3, a SNP site 4, a SNP site 5, a SNP site 6, a SNP site 7 and a SNP site 8, which are located in tea genomes Scaffold4239:309117, Scaffold3614: 66549, Scaffold349: 3413816, Scaffold1989: 2316385, Scaffold451: 940283, Scaffold3727:442660, Scaffold115:803980 and Scaffold920:281727, respectively, which are a 501st base of a nucleotide sequence shown in SEQ ID NO: 1, a 501st base of a nucleotide sequence shown in SEQ ID NO:4, a 501st base of a nucleotide sequence shown in SEQ ID NO:7, a 501st base of a nucleotide sequence shown in SEQ ID NO: 10, a 501st base of a nucleotide sequence shown in SEQ ID NO: 13, a 501st base of a nucleotide sequence shown in SEQ ID NO: 16, a 501st base of a nucleotide sequence shown in SEQ ID NO: 19, and a 501st base of a nucleotide sequence shown in SEQ ID NO:22.

The second objective of the present invention is to provide use of any one or more molecular marker of the molecular marker combination in evaluating the tea plant (+)-catechin content.

The third objective of the present invention is to provide use of primers of any one or more molecular marker of the molecular marker combination in evaluating the tea plant (+)-catechin content.

The fourth objective of the present invention is to provide primers for detecting SNP site 1.

The fifth objective of the present invention is to provide primers for detecting SNP site 2.

The sixth objective of the present invention is to provide primers for detecting SNP site 3.

The seventh objective of the present invention is to provide primers for detecting SNP site 4.

The eighth objective of the present invention is to provide primers for detecting SNP site 5.

The ninth objective of the present invention is to provide primers for detecting SNP site 6.

The tenth objective of the present invention is to provide primers for detecting SNP site 7.

The eleventh objective of the present invention is to provide primers for detecting SNP site 8.

The twelfth objective of the present invention is to provide a kit for evaluating tea plant (+)-catechin content.

The thirteenth objective of the present invention is to provide a method for evaluating tea plant (+)-catechin content.

The fourteenth objective of the present invention is to provide use of any one or more of any one or more molecular marker in the molecular marker combination, the primers for the SNP site 1, the primers for the SNP site 2, the primers for the SNP site 3, the primers for the SNP site 4, the primers for the SNP site 5, the primers for the SNP site 6, the primers for the SNP site 7, the primers for the SNP site 8, or the kit in molecular-assisted breeding.

In order to achieve the above objectives, the present invention is realized by the following technical solutions.

After a long period of exploratory research, the inventors discovered eight SNP site molecular markers linked to (+)-catechin content. It is further used to establish a detection method for detecting the sites, which can be used to evaluate the tea plant (+)-catechin content, for further use in resource screening and molecular breeding.

Therefore, the present invention claims a molecular marker combination linked to quantitative traits of tea plant (+)-catechin content, including a SNP site 1, a SNP site 2, a SNP site 3, a SNP site 4, a SNP site 5, a SNP site 6, a SNP site 7 and a SNP site 8, which are located in tea genomes Scaffold4239:309117, Scaffold3614: 66549, Scaffold349: 3413816, Scaffold1989: 2316385, Scaffold451: 940283, Scaffold3 727:442660, Scaffold115:803980 and Scaffold920:281727, respectively, i.e., a 501st base of a nucleotide sequence shown in SEQ ID NO:1, a 501st base of a nucleotide sequence shown in SEQ ID NO:4, a 501st base of a nucleotide sequence shown in SEQ ID NO:7, a 501 st base of a nucleotide sequence shown in SEQ ID NO:10, a 501st base of a nucleotide sequence shown in SEQ ID NO:13, a 501st base of a nucleotide sequence shown in SEQ ID NO: 16, a 501st base of a nucleotide sequence shown in SEQ ID NO: 19, and a 501st base of a nucleotide sequence shown in SEQ ID NO:22.

The SNP site 1 is located in the tea genome Scaffold4239: 309117 (i.e. the 501st base of the nucleotide sequence shown in SEQ ID NO:1), this site is G or A, and genotype thereof is extremely significantly correlated with the (+)-catechin content in the dry matter of the tea plant. It is shown by correlation analysis and significance analysis verification that the (+)-catechin content in the dry matter of tea soup corresponding to an AA genotype sample has extremely significant difference compared with GG and GA genotype samples. It is statistically judged that, when the genotype of the sample is double mutant AA, the catechin content in the dry matter in the tea plant is more likely to be higher than the normal average of the sample of which the genotype is wild type GG or single mutant GA.

The SNP site 2 is located in the tea genome Scaffold3614: 66549 (i.e. the 501st base of the nucleotide sequence shown in SEQ ID NO:4), this site is T or C, and genotype thereof is extremely significantly correlated with the (+)-catechin content in the dry matter of the tea plant. It is shown by correlation analysis and significance analysis verification that the (+)-catechin content in the dry matter corresponding to a CC genotype sample has extremely significant difference compared with TT and CT genotype samples. It is statistically judged that, when the genotype of the sample is double mutant CC, the (+)-catechin content in the dry matter in the tea plant is more likely to be higher than the sample of which the genotype is wild type TT or single mutant CT.

The SNP site 3 is located in the tea genome Scaffold349: 3413816 (i.e. the 501st base of the nucleotide sequence shown in SEQ ID NO:7), this site is G or A, and genotype thereof is extremely significantly correlated with the (+)-catechin content in the dry matter of the tea plant. It is shown by correlation analysis and significance analysis verification that the (+)-catechin content in the dry matter of tea soup corresponding to a GG genotype sample has extremely significant difference compared with GA and AA genotype samples. It is statistically judged that, when the genotype of the sample is double mutant GG, the (+)-catechin content in the dry matter in the tea plant is more likely to be higher than the sample of which the genotype is wild type AA or single mutant GA.

The SNP site 4 is located in the tea genome Scaffold1989: 2316385 (i.e. the 501st base of the nucleotide sequence shown in SEQ ID NO: 10), this site is G or A, and genotype thereof is extremely significantly correlated with the (+)-catechin content in the dry matter of the tea plant. It is shown by correlation analysis and significance analysis verification that the (+)-catechin content in the dry matter of tea soup corresponding to an AA genotype sample has extremely significant difference compared with GA and GG genotype samples. It is statistically judged that, when the genotype of the sample is double mutant AA, the (+)-catechin content in the dry matter in the tea plant is more likely to be higher than the normal average of the sample of which the genotype is wild type GG or single mutant GA.

The SNP site 5 is located in the tea genome Scaffold451: 940283 (i.e. the 501st base of the nucleotide sequence shown in SEQ ID NO:13), this site is C or T, and genotype thereof is extremely significantly correlated with the (+)-catechin content in the dry matter of the tea plant. It is shown by correlation analysis and significance analysis verification that the (+)-catechin content in the dry matter of tea soup corresponding to a TT genotype sample has extremely significant difference compared with CC and CT genotype samples. It is statistically judged that, when the genotype of the sample is double mutant TT, the (+)-catechin content in the dry matter in the tea plant is more likely to be higher than the normal average of the sample of which the genotype is wild type CC or single mutant CT.

The SNP site 6 is located in the tea genome Scaffold3727: 442660 (i.e. the 501st base of the nucleotide sequence shown in SEQ ID NO: 16), this site is G or A, and genotype thereof is extremely significantly correlated with the (+)-catechin content in the dry matter of the tea plant. It is shown by correlation analysis and significance analysis verification that the (+)-catechin content in the dry matter of tea soup corresponding to an AA genotype sample has extremely significant difference compared with GG and GA genotype samples. It is statistically judged that, when the genotype of the sample is double mutant AA, the (+)-catechin content in the dry matter in the tea plant is more likely to be higher than the normal average of the sample of which the genotype is wild type GG or single mutant GA.

The SNP site 7 is located in the tea genome Scaffold115: 803980 (i.e. the 501st base of the nucleotide sequence shown in SEQ ID NO:19), this site is G or A, and genotype thereof is extremely significantly correlated with the (+)-catechin content in the dry matter of the tea plant. It is shown by correlation analysis and significance analysis verification that the (+)-catechin content in the dry matter of the tea plant corresponding to a GG genotype sample has extremely significant difference compared with AA and GA genotype samples, it is statistically judged that, when the genotype of the sample is double mutant GG, the (+)-catechin content in the dry matter in the tea plant is more likely to be higher than the sample of which the genotype is wild type AA or single mutant GA.

The SNP site 8 is located in the tea genome Scaffold920: 281727 (i.e. the 501st base of the nucleotide sequence shown in SEQ ID NO:22), this site is G or A, and genotype thereof is extremely significantly correlated with the (+)-catechin content in the dry matter of the tea plant. It is shown by correlation analysis and significance analysis verification that the (+)-catechin content in the dry matter of the tea plant corresponding to a GG genotype sample has extremely significant difference compared with AA and GA genotype samples, it is statistically judged that, when the genotype of the sample is double mutant GG, the (+)-catechin content in the dry matter in the tea plant is more likely to be higher than the sample of which the genotype is wild type AA or single mutant GA.

The tea plant (+)-catechin content according to the present invention is specifically a proportion of (+)-catechin in dry matter of fresh tea leaves.

Use of any one or more molecular marker of the molecular marker combination in evaluating the tea plant (+)-catechin content also belongs to the scope of protection of the present invention.

The present invention further claims use of primers of any one or more molecular marker of the molecular marker combination in evaluating the tea plant (+)-catechin content.

Primers for the SNP site 1, wherein nucleotide sequences thereof are shown as SEQ ID NO: 2 and SEQ ID NO: 3.

```
primer F:
                                       (SEQ ID NO: 2)
GAAGACTAACCCGTATCGAG;

primer R:
                                       (SEQ ID NO: 3)
ACACTTACAGTCTCTTGCGG.
```

Primers for the SNP site 2, wherein nucleotide sequences thereof are shown as SEQ ID NO: 5 and SEQ ID NO: 6.

```
primer F:
                                       (SEQ ID NO: 5)
GATGACACAACCCTCATCTG;

primer R:
                                       (SEQ ID NO: 6)
AATGTATGCCCGGTAAGGAC.
```

Primers for the SNP site 3, wherein nucleotide sequences thereof are shown as SEQ ID NO: 8 and SEQ ID NO: 9.

```
primer F:
                                       (SEQ ID NO: 8)
TCTCTGCACTGTTGTCACTC;

primer R:
                                       (SEQ ID NO: 9)
CACCACACTTTCTTAGAAGG.
```

Primers for the SNP site 4, wherein nucleotide sequences thereof are shown as SEQ ID NO: 11 and SEQ ID NO: 12.

```
primer F:
                                       (SEQ ID NO: 11)
GATTTGACCTTCAACGTGGG;

primer R:
                                       (SEQ ID NO: 12)
TGCAGCGTTTGTGTTTGCAG.
```

Primers for the SNP site 5, wherein nucleotide sequences thereof are shown as SEQ ID NO: 14 and SEQ ID NO: 15.

```
primer F:
                                       (SEQ ID NO: 14)
GTAATAGACGGTGCAAACCC;

primer R:
                                       (SEQ ID NO: 15)
CAAAGTATTTGGGAGCGCTG.
```

Primers for the SNP site 6, wherein nucleotide sequences thereof are shown as SEQ ID NO: 17 and SEQ ID NO: 18.

```
primer F:
                                       (SEQ ID NO: 17)
TTGTCCGTGTCCAATCCTTG;

primer R:
                                       (SEQ ID NO: 18)
ATTGACCACCTGGAAGAAGC.
```

Primers for the SNP site 7, wherein nucleotide sequences thereof are shown as SEQ ID NO: 20 and SEQ ID NO: 21.

```
primer F:
                                       (SEQ ID NO: 20)
CTTCATCTCCACCACACTTC;

primer R:
                                       (SEQ ID NO: 21)
GCCCAAAGTAGCAAAGAGAG.
```

Primers for the SNP site 8, wherein nucleotide sequences thereof are shown as SEQ ID NO: 23 and SEQ ID NO: 24.

```
primer F:
                                       (SEQ ID NO: 23)
TTCGCATTCGTCCTTTTGGG;

primer R:
                                       (SEQ ID NO: 24)
ACGTGCTACATTCTCCATCC.
```

Further, the present invention claims a kit for evaluating tea plant (+)-catechin content, including a reagent for detecting the molecular marker combination or any one molecular marker thereof.

Preferably, the reagent is the primers for the SNP site 1 which have the nucleotide sequences shown as SEQ ID NO: 2 and SEQ ID NO: 3, the primers for the SNP site 2 which have the nucleotide sequences shown as SEQ ID NO: 5 and SEQ ID NO: 6, the primers for the SNP site 3 which have the nucleotide sequences shown as SEQ ID NO: 8 and SEQ ID NO: 9, the primers for the SNP site 4 which have the nucleotide sequences shown as SEQ ID NO: 11 and SEQ ID NO: 12, the primers for the SNP site 5 which have the nucleotide sequences shown as SEQ ID NO: 14 and SEQ ID NO: 15, the primers for the SNP site 6 which have the nucleotide sequences shown as SEQ ID NO: 17 and SEQ ID NO: 18, the primers for the SNP site 7 which have the nucleotide sequences shown as SEQ ID NO: 20 and SEQ ID NO: 21, and/or the primers for the SNP site 8 which have the nucleotide sequences shown as SEQ ID NO: 23 and SEQ ID NO: 24.

The most preferably, the kit contains the primers for the SNP site 1 have the nucleotide sequences shown as SEQ ID NO: 2 and SEQ ID NO: 3, the primers for the SNP site 2 have the nucleotide sequences shown as SEQ ID NO: 5 and SEQ ID NO: 6, the primers for the SNP site 3 have the nucleotide sequences shown as SEQ ID NO: 8 and SEQ ID NO: 9, the primers for the SNP site 4 have the nucleotide sequences shown as SEQ ID NO: 11 and SEQ ID NO: 12, the primers for the SNP site 5 have the nucleotide sequences shown as SEQ ID NO: 14 and SEQ ID NO: 15, and/or the primers for the SNP site 6 have the nucleotide sequences shown as SEQ ID NO: 17 and SEQ ID NO: 18, the primers for the SNP site 7 have the nucleotide sequences shown as SEQ ID NO: 20 and SEQ ID NO: 21, the primers for the SNP site 8 have the nucleotide sequences shown as SEQ ID NO: 23 and SEQ ID NO: 24, 2×Taq PCR Master Mix, and ddH$_2$O.

A usage method is as follows:

(1) CTAB method is used to extract total DNA from buds of tea plant, it is ensured that A260/A280 of each DNA sample is between 1.8 and 2.0, and the concentration is greater than 100 μg/μl;

(2) PCR amplification

PCR system (10 μl) is as follows:

| 2 × Taq PCR Master Mix | 5 μl |
| primers | Each 0.5 μl |
| DNA template | 1 μl |
| ddH$_2$O | 3 μl |

PCR amplification procedure is as follows:

| 95° C. | 5 minutes | |
| 95° C. | 30 seconds | ×45 cycles |
| 56° C. | 30 seconds | |
| 72° C. | 30 seconds | |
| 72° C. | 2 minutes | |
| 4° C. | forever | |

(3) Product purification

The PCR amplification products are subjected to gel electrophoresis, followed by recovery and purification using a commercially available gel electrophoresis DNA recovery kit.

A band with a fragment length of about 240 bp in the amplification product of the primers shown in SEQ ID NO: 2 and SEQ ID NO: 3 is selected for recovery and purification.

A band with a fragment length of about 240 bp in the amplification product of the primers shown in SEQ ID NO: 5 and SEQ ID NO: 6 is selected for recovery and purification.

A band with a fragment length of about 240 bp in the amplification product of the primers shown in SEQ ID NO: 8 and SEQ ID NO: 9 is selected for recovery and purification.

A band with a fragment length of about 240 bp in the amplification product of the primers shown in SEQ ID NO: 11 and SEQ ID NO: 12 is selected for recovery and purification.

A band with a fragment length of about 240 bp in the amplification product of the primers shown in SEQ ID NO: 14 and SEQ ID NO: 15 is selected for recovery and purification.

A band with a fragment length of about 240 bp in the amplification product of the primers shown in SEQ ID NO: 17 and SEQ ID NO: 18 is selected for recovery and purification.

A band with a fragment length of about 240 bp in the amplification product of the primers shown in SEQ ID NO: 20 and SEQ ID NO: 21 is selected for recovery and purification.

A band with a fragment length of about 240 bp in the amplification product of the primers shown in SEQ ID NO: 23 and SEQ ID NO: 24 is selected for recovery and purification.

(4) Sequencing and interpretation of results

The recovered and purified product is sent to a sequencing company for Sanger sequencing. At the site Scaffold4239: 309117, it is statistically judged that, when the genotype of the sample is double mutant AA, the (+)-catechin content in the dry matter in the tea plant is more likely to be higher than the normal average of the sample of which the genotype is wild type GG or single mutant GA.

At the site Scaffold3614: 66549, when the genotype is double mutant CC, the (+)-catechin content in the tea plant is more likely to be higher than the normal average of CT and TT genotype resources.

At the site Scaffold349: 3413816, when the genotype is double mutant GG, the (+)-catechin content in the tea plant is more likely to be higher than the normal average of AA and GA genotype resources.

At the site Scaffold1989: 2316385, when the genotype is double mutant AA, the (+)-catechin content in the tea plant is more likely to be higher than the normal average of GG and GA genotype resources.

At the site Scaffold451: 940283, it is statistically judged that, when the genotype of the sample is double mutant TT, the (+)-catechin content in the dry matter in the tea plant is more likely to be higher than the normal average of the sample of which the genotype is wild type CC or single mutant CT.

At the site Scaffold3727:442660, it is statistically judged that, when the genotype of the sample is double mutant AA, the (+)-catechin content in the dry matter in the tea plant is more likely to be higher than the normal average of the sample of which the genotype is wild type GG or single mutant GA.

At the site Scaffold115: 803980, it is statistically judged that, when the genotype of the sample is double mutant GG, the (+)-catechin content in the dry matter in the tea plant is more likely to be higher than the sample of which the genotype is wild type AA or single mutant GA.

At the site Scaffold920: 281727, it is statistically judged that, when the genotype of the sample is double mutant GG, the (+)-catechin content in the dry matter in the tea plant is more likely to be higher than the sample of which the genotype is wild type AA or single mutant GA.

In the meantime, the present invention claims a method for evaluating the tea plant (+)-catechin content, which detects a genotype of any one or more molecular marker of the molecular marker combination.

Use of any one or more of any one or more molecular markers of the molecular marker combination, the primers for the SNP site 1, the primers for the SNP site 2, the primers for the SNP site 3, the primers for the SNP site 4, the primers for the SNP site 5, the primers for the SNP site 6, the primers for the SNP site 7, the primers for the SNP site 8, or the kit in molecular-assisted breeding.

Compared with the prior art, the present invention has the following beneficial effects.

The present invention first discovered the following.

The SNP site 1 is located in the tea genome Scaffold4239: 309117, this site is G or A, and genotype thereof is extremely significantly correlated with the (+)-catechin content in the dry matter of the tea plant. It is shown by correlation analysis and significance analysis verification that the (+)-catechin content in the dry matter of tea soup corresponding to an AA genotype sample has extremely significant difference compared with GG and GA genotype samples. It is statistically judged that, when the genotype of the sample is double mutant AA, the catechin content in the dry matter in the tea plant is more likely to be higher than the normal average of the sample of which the genotype is wild type GG or single mutant GA.

SNP site 2 is located in the tea genome Scaffold3614: 66549, this site is T or C, and genotype thereof is extremely significantly correlated with the (+)-catechin content in the dry matter of the tea plant. It is shown by correlation analysis and significance analysis verification that the (+)-catechin content in the dry matter corresponding to a CC genotype sample has extremely significant difference compared with TT and CT genotype samples. It is statistically judged that, when the genotype of the sample is double mutant CC, the (+)-catechin content in the dry matter in the tea plant is more likely to be higher than the sample of which the genotype is wild type TT or single mutant CT.

SNP site 3 is located in the tea genome Scaffold349: 3413816, this site is G or A, and genotype thereof is extremely significantly correlated with the (+)-catechin content in the dry matter of the tea plant. It is shown by correlation analysis and significance analysis verification that the (+)-catechin content in the dry matter of tea soup corresponding to a GG genotype sample has extremely significant difference compared with GA and AA genotype samples. It is statistically judged that, when the genotype of the sample is double mutant GG, the (+)-catechin content in the dry matter in the tea plant is more likely to be higher than the sample of which the genotype is wild type AA or single mutant GA.

SNP site 4 is located in the tea genome Scaffold1989: 2316385, this site is G or A, and genotype thereof is extremely significantly correlated with the (+)-catechin content in the dry matter of the tea plant. It is shown by correlation analysis and significance analysis verification that the (+)-catechin content in the dry matter of tea soup corresponding to an AA genotype sample has extremely significant difference compared with GA and GG genotype samples. It is statistically judged that, when the genotype of the sample is double mutant AA, the (+)-catechin content in the dry matter in the tea plant is more likely to be higher than the normal average of the sample of which the genotype is wild type GG or single mutant GA.

SNP site 5 is located in the tea genome Scaffold451: 940283, this site is C or T, and genotype thereof is extremely significantly correlated with the (+)-catechin content in the dry matter of the tea plant. It is shown by correlation analysis and significance analysis verification that the (+)-catechin content in the dry matter of tea soup corresponding to a TT genotype sample has extremely significant difference compared with CC and CT genotype samples. It is statistically judged that, when the genotype of the sample is double mutant TT, the (+)-catechin content in the dry matter in the tea plant is more likely to be higher than the normal average of the sample of which the genotype is wild type CC or single mutant CT.

SNP site 6 is located in the tea genome Scaffold3727: 442660, this site is G or A, and genotype thereof is extremely significantly correlated with the (+)-catechin content in the dry matter of the tea plant. It is shown by correlation analysis and significance analysis verification that the (+)-catechin content in the dry matter of tea soup corresponding to an AA genotype sample has extremely significant difference compared with GG and GA genotype samples. It is statistically judged that, when the genotype of the sample is double mutant AA, the (+)-catechin content in the dry matter in the tea plant is more likely to be higher than the normal average of the sample of which the genotype is wild type GG or single mutant GA.

SNP site 7 is located in the tea genome Scaffold 115: 803980, this site is G or A, and genotype thereof is extremely significantly correlated with the (+)-catechin content in the dry matter of the tea plant. It is shown by correlation analysis and significance analysis verification that the (+)-catechin content in the dry matter of the tea plant corresponding to a GG genotype sample has extremely significant difference compared with AA and GA genotype samples, it is statistically judged that, when the genotype of the sample is double mutant GG, the (+)-catechin content in the dry matter in the tea plant is more likely to be higher than the sample of which the genotype is wild type AA or single mutant GA.

SNP site 8 is located in the tea genome Scaffold920: 281727, this site is G or A, and genotype thereof is extremely significantly correlated with the (+)-catechin content in the dry matter of the tea plant. It is shown by correlation analysis and significance analysis verification that the (+)-catechin content in the dry matter of the tea plant corresponding to a GG genotype sample has extremely significant difference compared with AA and GA genotype samples, it is statistically judged that, when the genotype of the sample is double mutant GG, the (+)-catechin content in the dry matter in the tea plant is more likely to be higher than the sample of which the genotype is wild type AA or single mutant GA.

It is further established a detection method for detecting the eight SNP sites, which can be used to evaluate the (+)-catechin content of the tea plant, for further use in screening of tea plant resources and molecular breeding. This is the basis for molecular marker-assisted selective breeding for tea plant, which has great research value.

BRIEF DESCRIPTION OF THE DRAWINGS

FIG. 2 shows a schematic diagram of a site Scaffold4239: 309117 (as shown in SEQ ID NO:1) and primers, wherein N denotes a base to be tested at Scaffold4239:309117, and bold and underlined parts denote upstream and downstream primers (upstream primer as shown in SEQ ID NO:2, downstream primer: CCGCAAGAGACTGTAAGTGT (SEQ ID NO:25)).

FIG. 3 shows a schematic diagram of a site Scaffold3614: 66549 (as shown in SEQ ID NO:4) and primers, wherein N denotes a base to be tested at Scaffold3614: 66549, and bold and underlined parts denote upstream and downstream primers (upstream primer as shown in SEQ ID NO:5, downstream primer: GTCCTTACCGGGCATACATT (SEQ ID NO:26)).

FIG. 4 shows a schematic diagram of a site Scaffold349: 3413816 (as shown in SEQ ID NO:7) and primers, wherein N denotes a base to be tested at Scaffold349: 3413816, and bold and underlined parts denote upstream and downstream primers (upstream primer as shown in SEQ ID NO:8, downstream primer: CCTTCTAAGAAAGTGTGGTG (SEQ ID NO:27)).

FIG. 5 shows a schematic diagram of a site Scaffold1989: 2316385 (as shown in SEQ ID NO:10) and primers, wherein N denotes a base to be tested at Scaffold1989: 2316385, and bold and underlined parts denote upstream and downstream primers (upstream primer as shown in SEQ ID NO:11, downstream primer: CTGCAAACACAAACGCTGCA (SEQ ID NO:28)).

FIG. 6 shows a schematic diagram of a site Scaffold451: 940283 (as shown in SEQ ID NO:13) and primers, wherein N denotes a base to be tested at Scaffold451: 940283, and bold and underlined parts denote upstream and downstream primers (upstream primer as shown in SEQ ID NO:14, downstream primer: CAGCGCTCCCAAATACTTTG (SEQ ID NO:29).

FIG. 7 shows a schematic diagram of a site Scaffold3727: 442660 (as shown in SEQ ID NO:16) and primers, wherein N denotes a base to be tested at Scaffold3727:442660, and bold and underlined parts denote upstream and downstream primers (upstream primer as shown in SEQ ID NO:17, downstream primer: GCTTCTTCCAGGTGGTCAAT (SEQ ID NO:30)).

FIG. 8 shows a schematic diagram of a site Scaffold115: 803980 (as shown in SEQ ID NO:19) and primers, wherein N denotes a base to be tested at Scaffold115: 803980, and bold and underlined parts denote upstream and downstream primers (upstream primer as shown in SEQ ID NO:20, downstream primer: CTCTCTTTGCTACTTTGGGC (SEQ ID NO:31)).

FIG. 9 shows a schematic diagram of a site Scaffold920: 281727 (as shown in SEQ ID NO:22) and primers, wherein N denotes a base to be tested at Scaffold920: 281727, and bold and underlined parts denote upstream and downstream primers (upstream primer as shown in SEQ ID NO:23, downstream primer: GGATGGAGAATGTAGCACGT (SEQ ID NO:32)).

FIG. 36 shows sequencing results of genotype at the site Scaffold349: 3413816 SEQ ID NO: 43: ATAAATAACAATATGTTTTTT).

FIG. 37 shows sequencing results of genotype at the site Scaffold115: 803980 (SEQ ID NO: 44: GATCCACGACA-CATCCCTCTT).

DETAILED DESCRIPTION OF THE INVENTION

Figure 1:
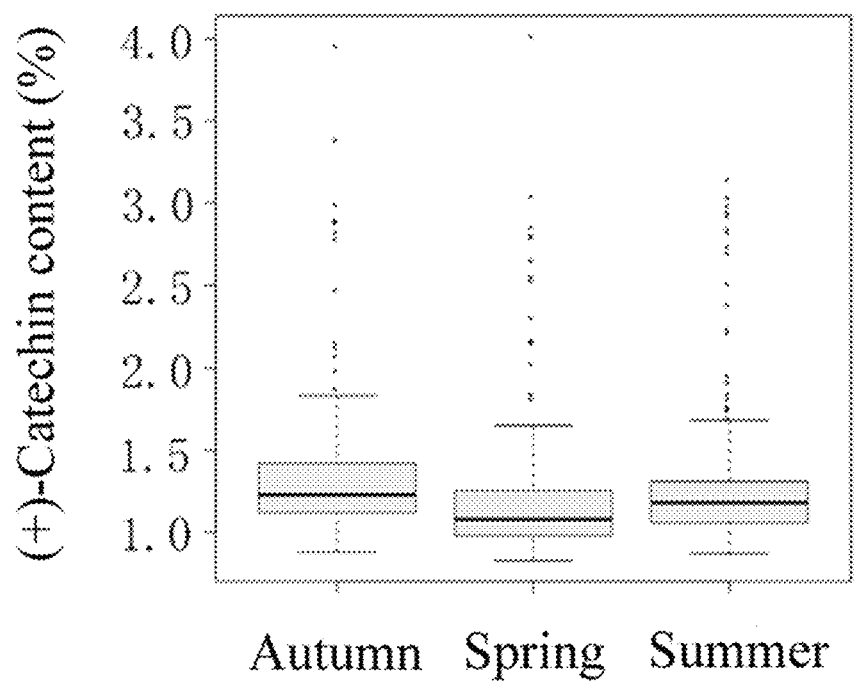
FIG. 1 shows (+)-catechin content in different seasons.
Figure 10:
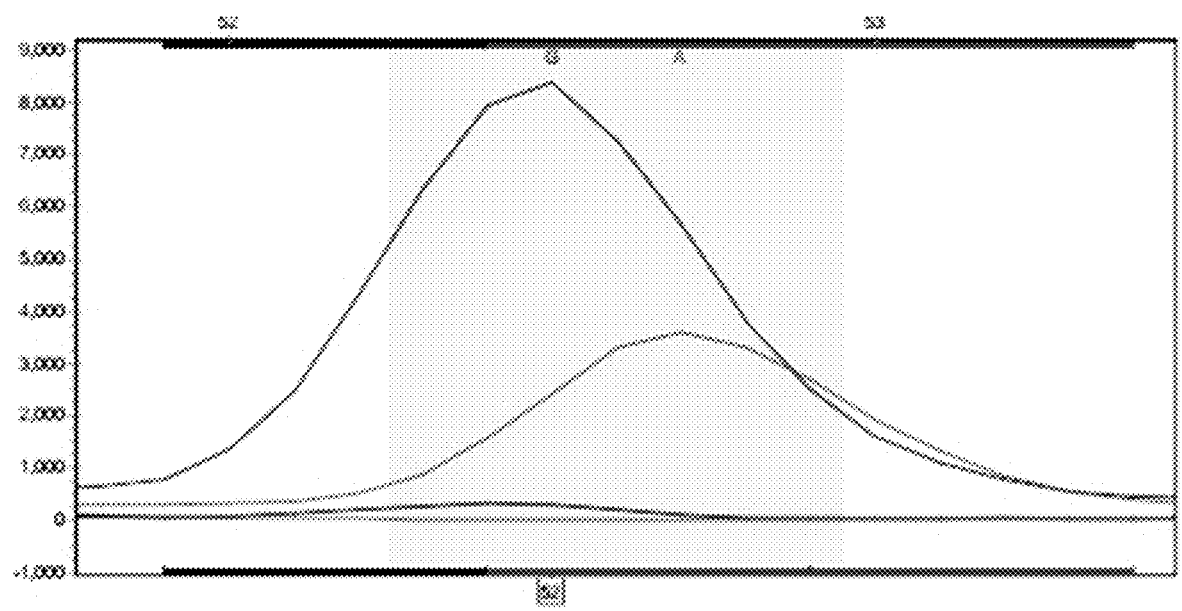
FIG. 10 shows SNAPshot sequencing results of genotype of the sample 2-72 at the site Scaffold4239:309117.
Figure 11:
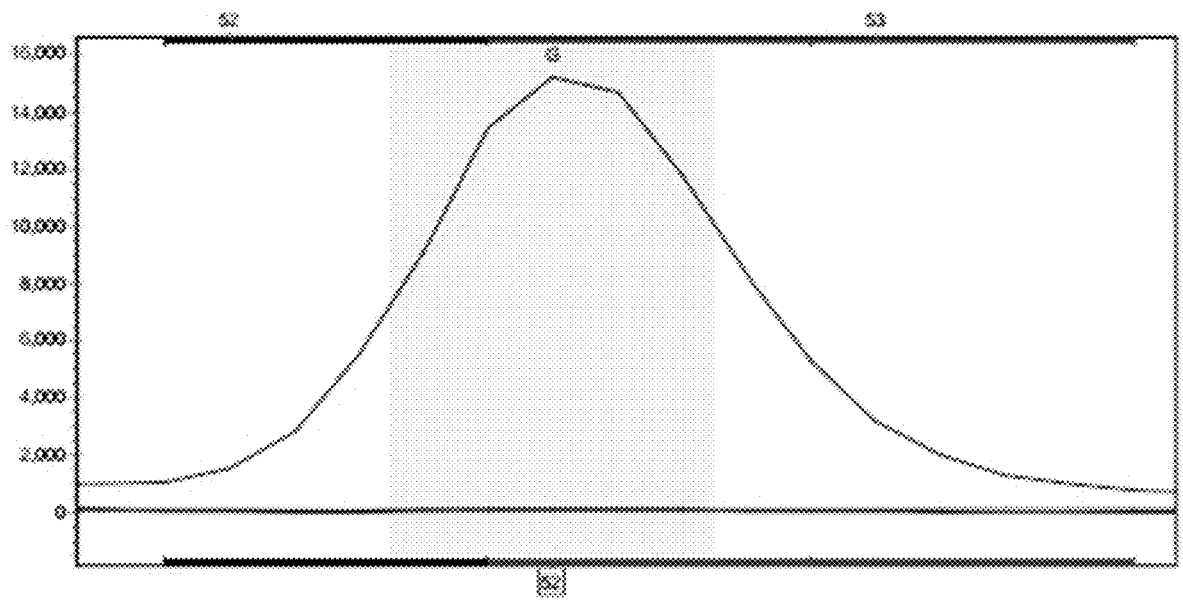
FIG. 11 shows SNAPshot sequencing results of genotype of the sample 2-78 at the site Scaffold4239:309117.
Figure 12:
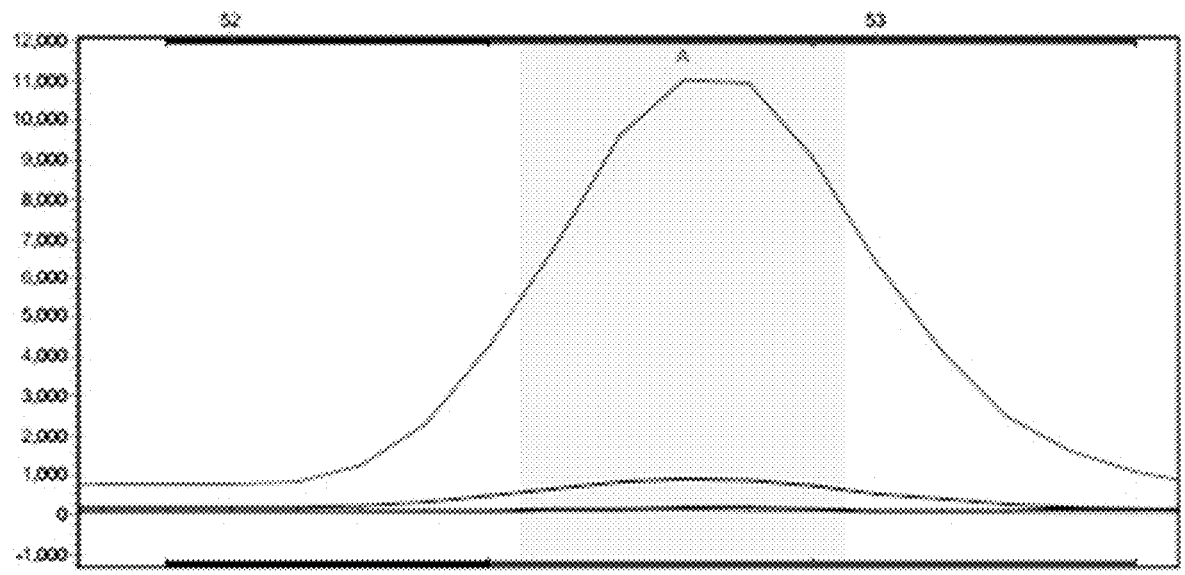
FIG. 12 shows SNAPshot sequencing results of genotype of the sample 2-97 at the site Scaffold4239:309117.
Figure 13:
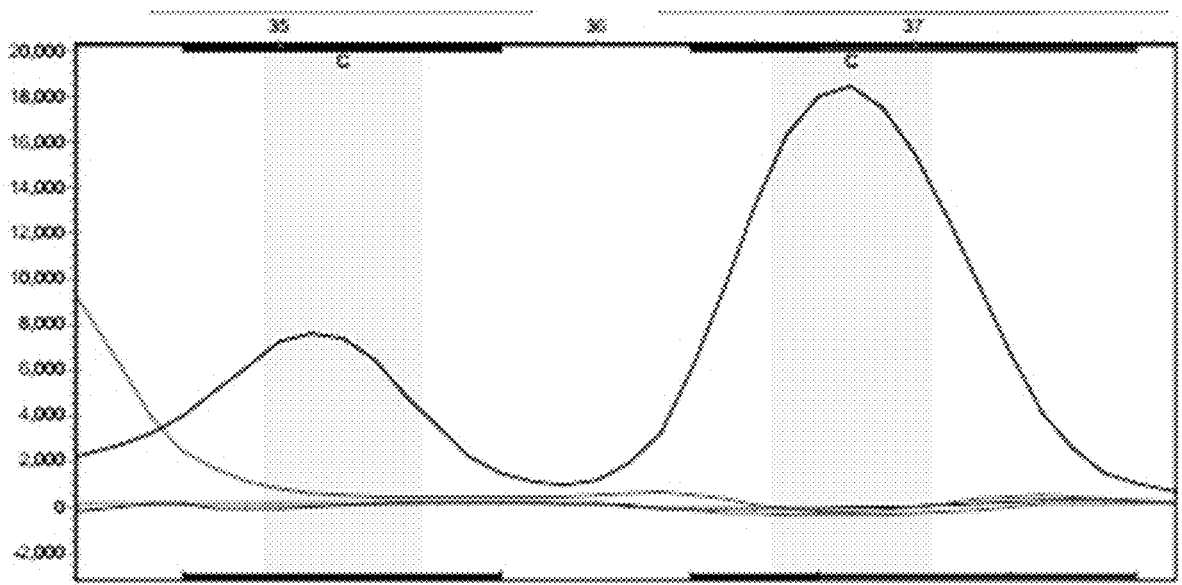
FIG. 13 shows SNAPshot sequencing results of genotype of the sample 2-62 at the site Scaffold1989: 2316385 (reverse compliment).
Figure 14:
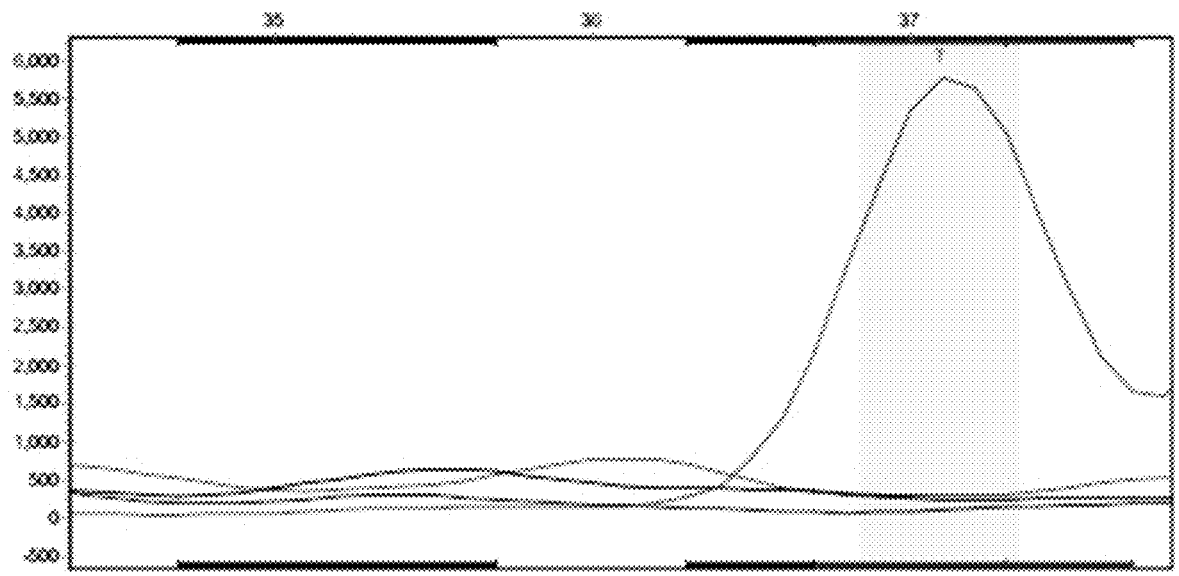
FIG. 14 shows SNAPshot sequencing results of genotype of the sample 2-77 at the site Scaffold1989: 2316385 (reverse compliment).
Figure 15:
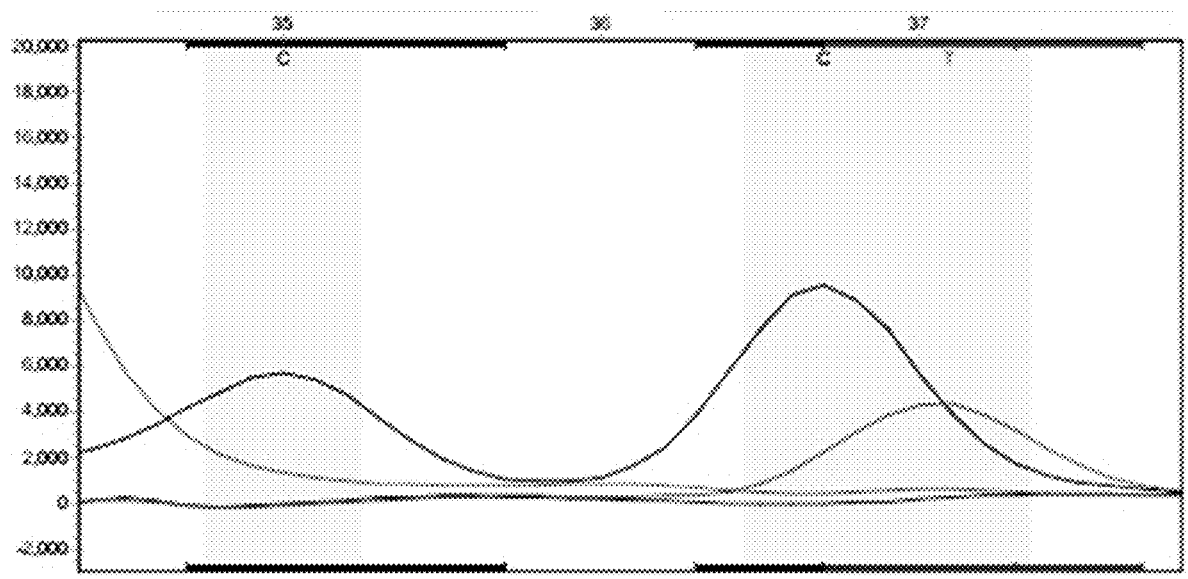
FIG. 15 shows SNAPshot sequencing results of genotype of the sample 2-69 at the site Scaffold1989: 2316385 (reverse compliment).
Figure 16:
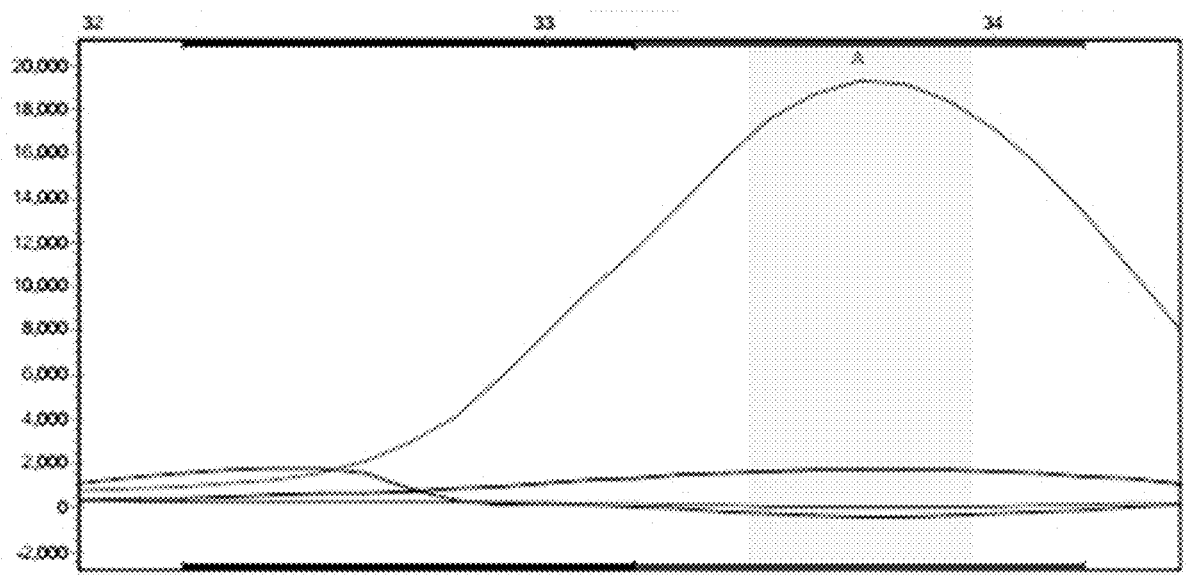
FIG. 16 shows SNAPshot sequencing results of genotype of the sample 2-22 at the site Scaffold3614: 66549 (reverse compliment).
Figure 17:
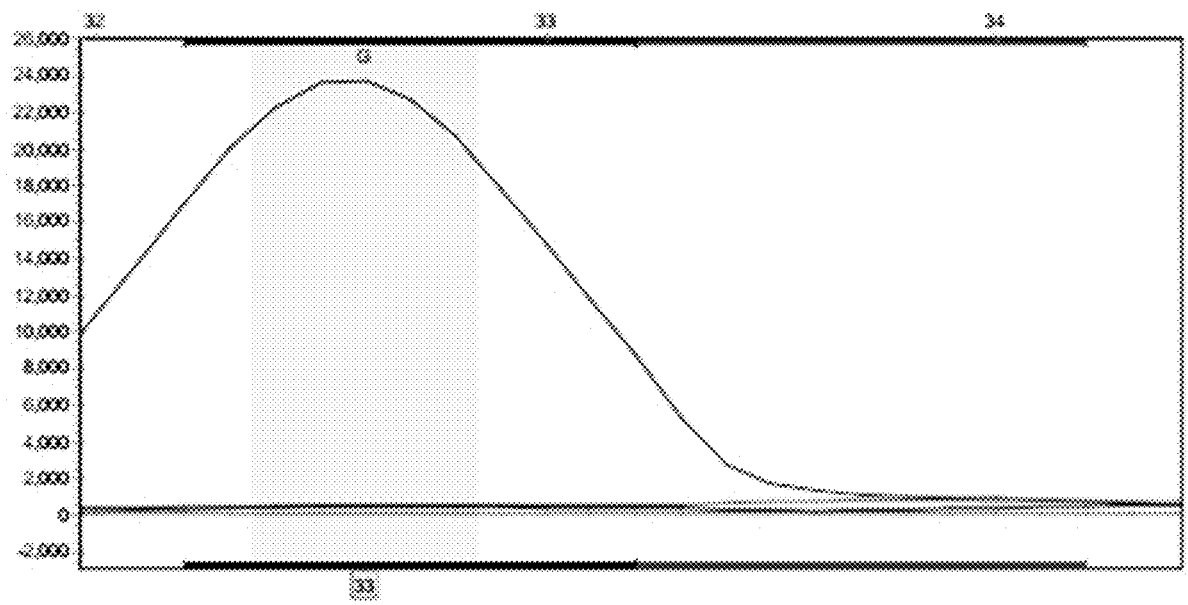
FIG. 17 shows SNAPshot sequencing results of genotype of the sample 2-14 at the site Scaffold3614: 66549 (reverse compliment).
Figure 18:
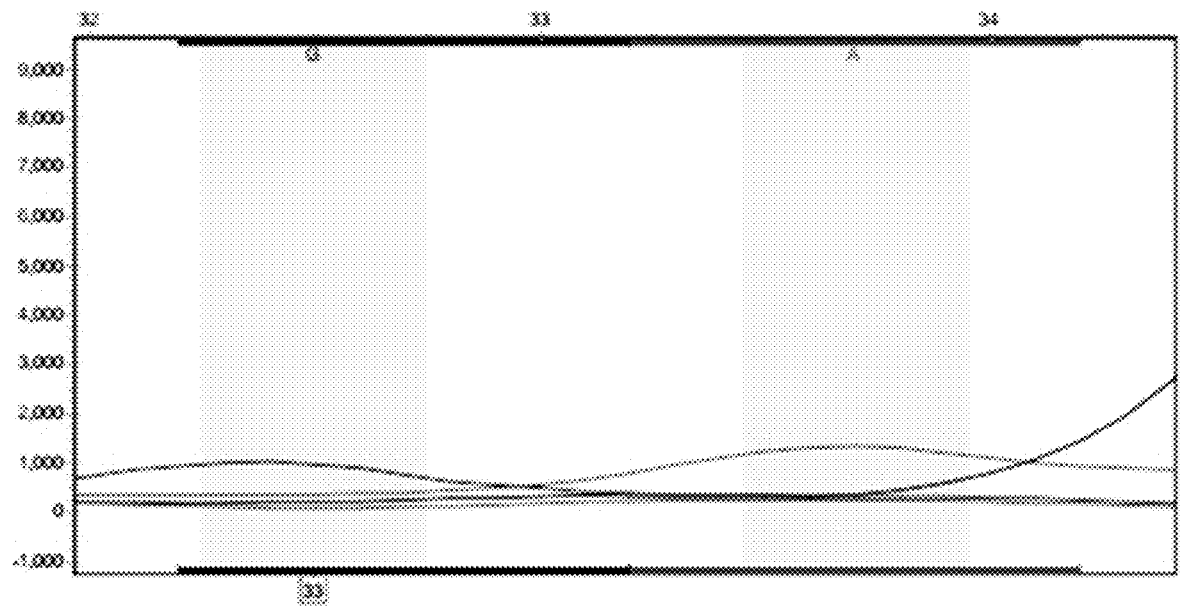
FIG. 18 shows SNAPshot sequencing results of genotype of the sample 2-24 at the site Scaffold3614: 66549 (reverse compliment).
Figure 19:
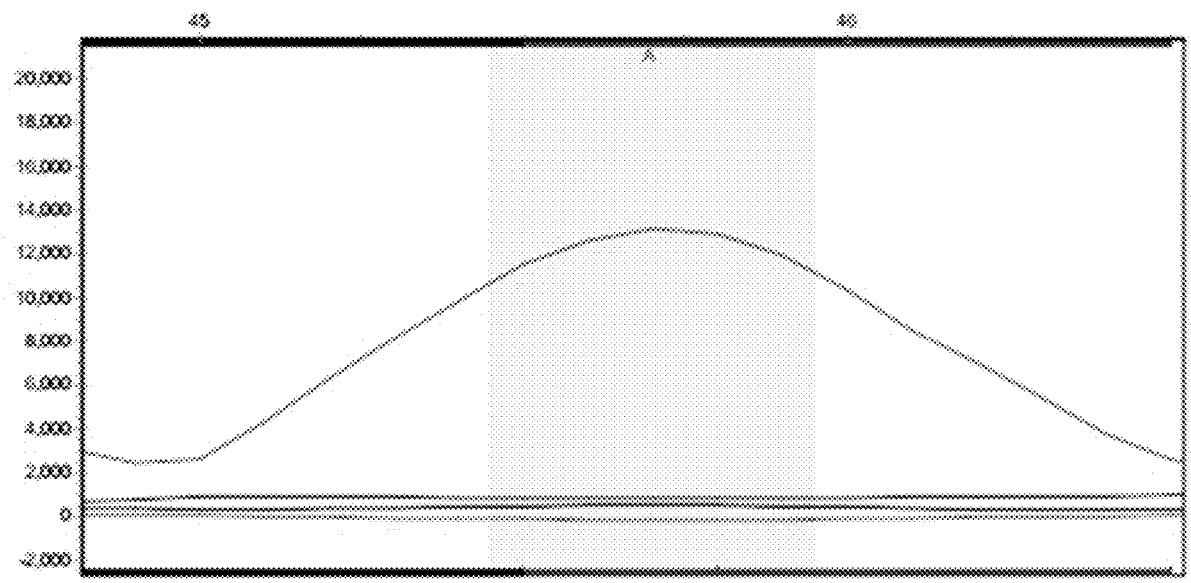
FIG. 19 shows SNAPshot sequencing results of genotype of the sample 2-15 at the site Scaffold349: 3413816.
Figure 20:
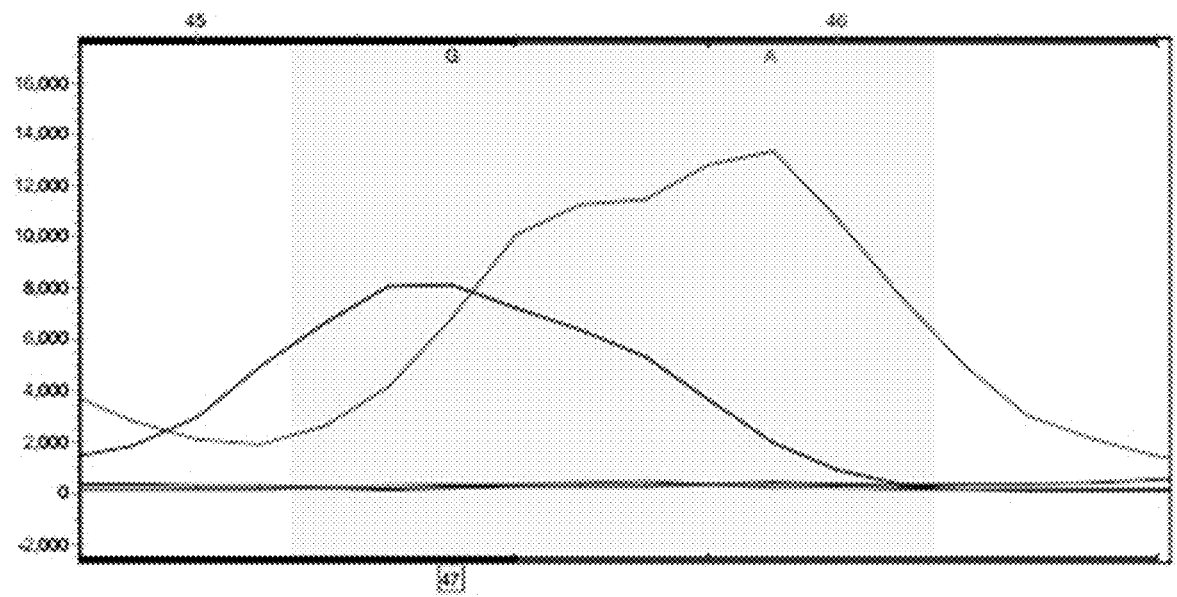
FIG. 20 shows SNAPshot sequencing results of genotype of the sample 2-19 at the site Scaffold349: 3413816.
Figure 21:
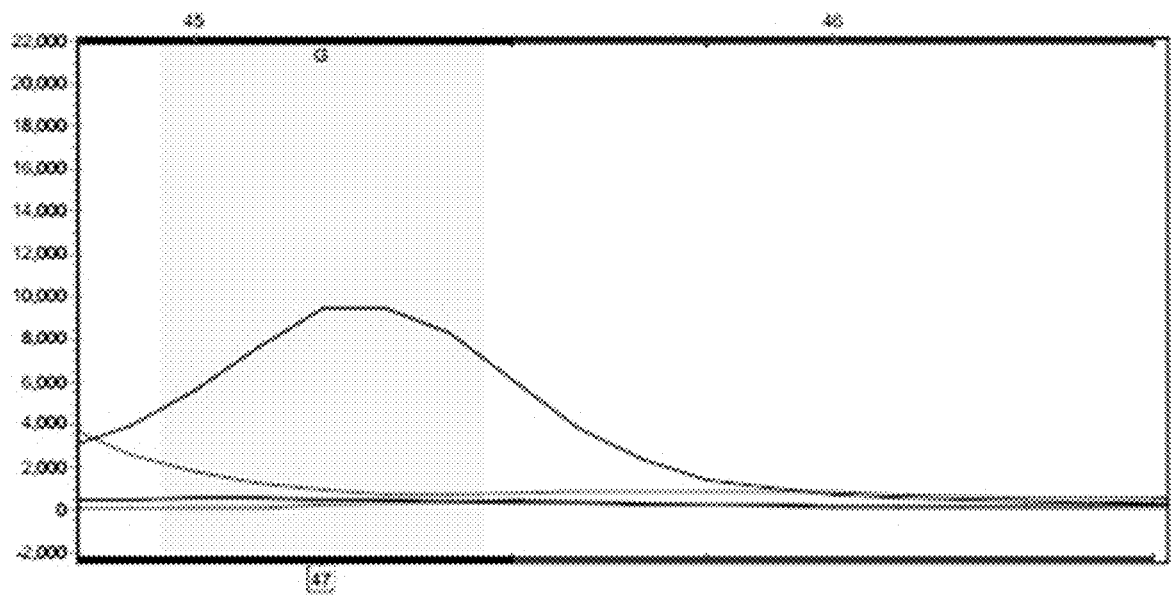
FIG. 21 shows SNapshot sequencing results of genotype of the sample 2-66 at the site Scaffold349: 3413816.
Figure 22:
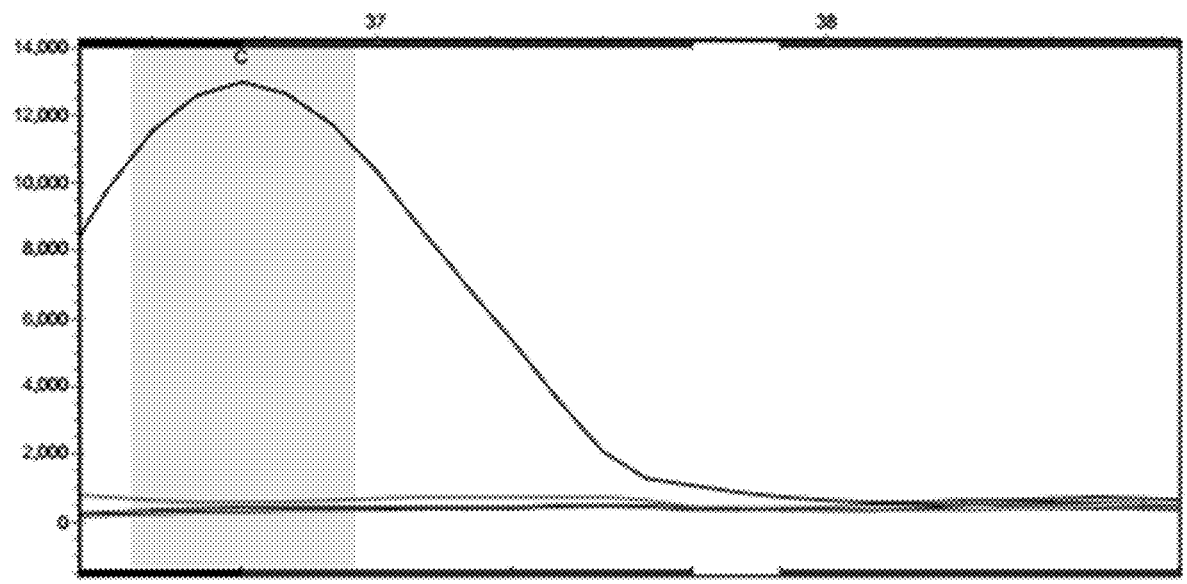
FIG. 22 shows SNAPshot sequencing results of genotype of the sample 2-92 at the site Scaffold451: 940283.
Figure 23:
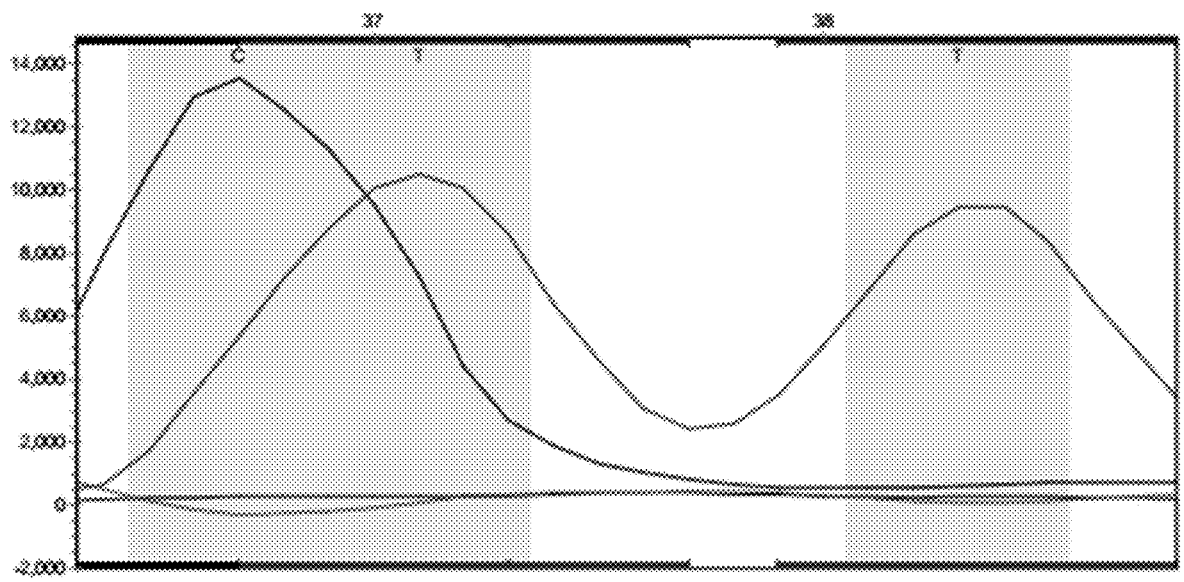
FIG. 23 shows SNAPshot sequencing results of genotype of the sample 2-77 at the site Scaffold451: 940283.
Figure 24:
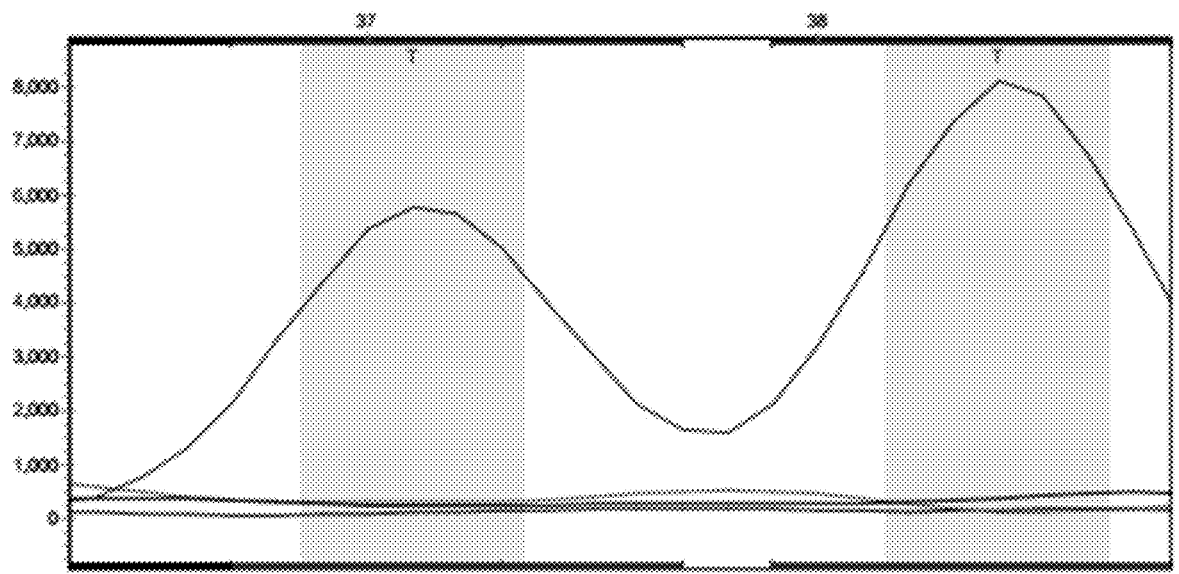
FIG. 24 shows SNAPshot sequencing results of genotype of the sample 2-97 at the site Scaffold451: 940283.
Figure 25:
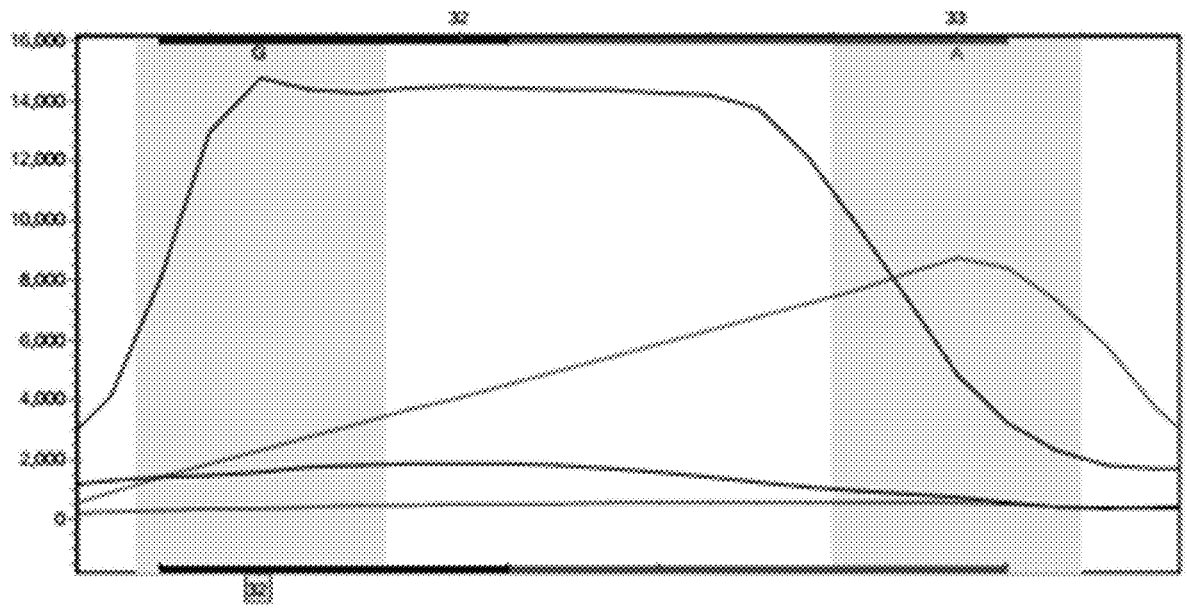
FIG. 25 shows SNAPshot sequencing results of genotype of the sample 2-51 at the site Scaffold3727:442660.
Figure 26:
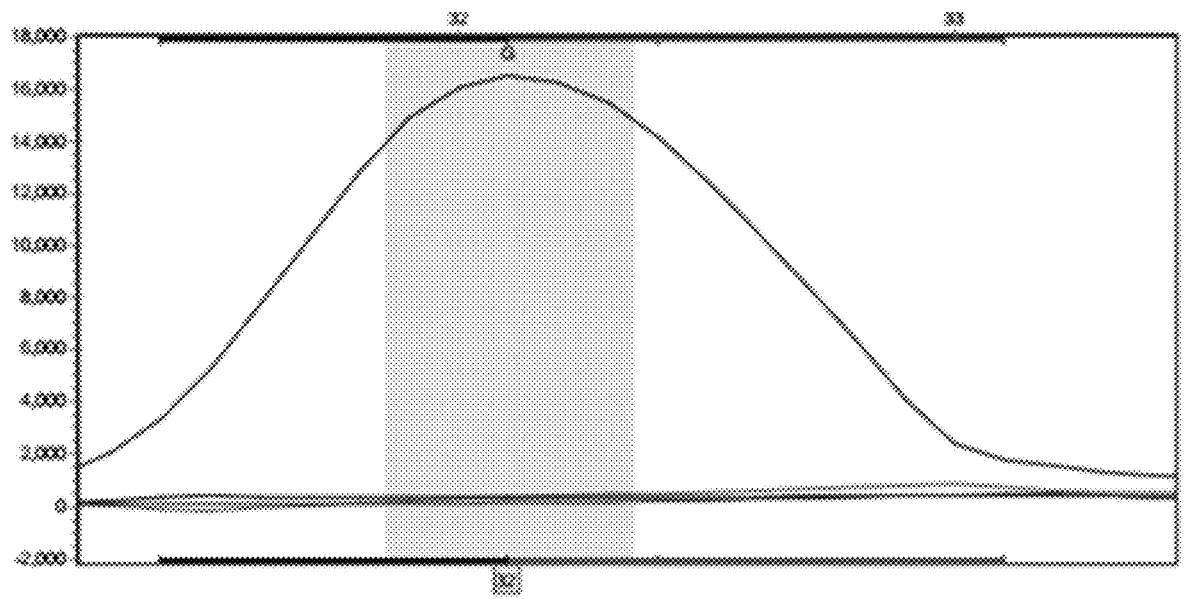
FIG. 26 shows SNAPshot sequencing results of genotype of the sample 2-35 at the site Scaffold3727:442660.
Figure 27:
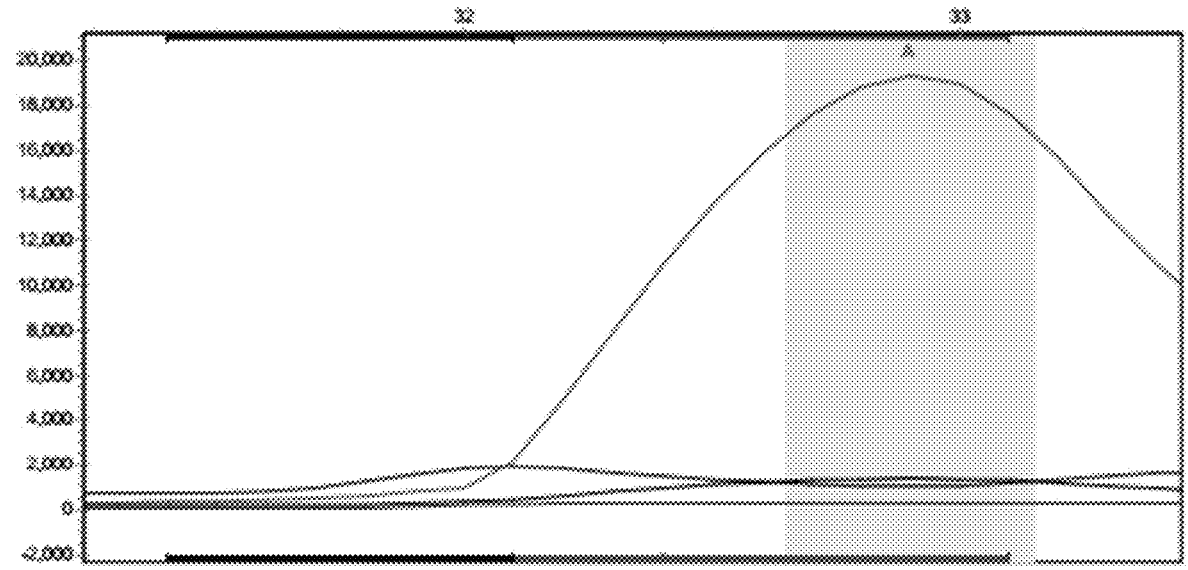
FIG. 27 shows SNAPshot sequencing results of genotype of the sample 2-44 at the site Scaffold3727:442660.
Figure 28:
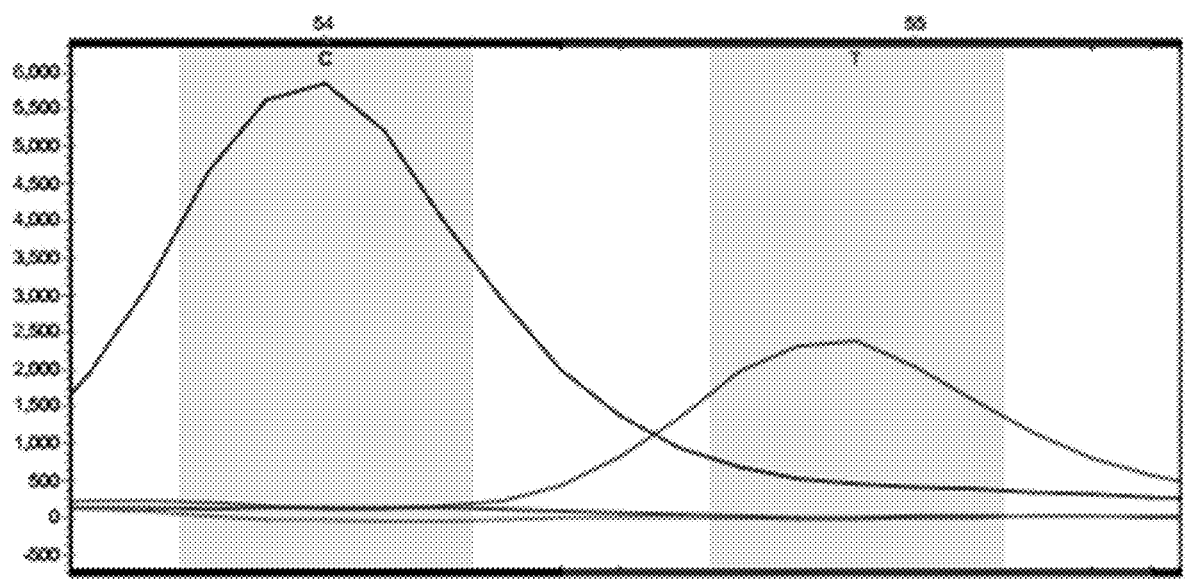
FIG. 28 shows SNAPshot sequencing results of genotype of the sample 2-50 at the site Scaffold115: 803980 (reverse compliment).
Figure 29:
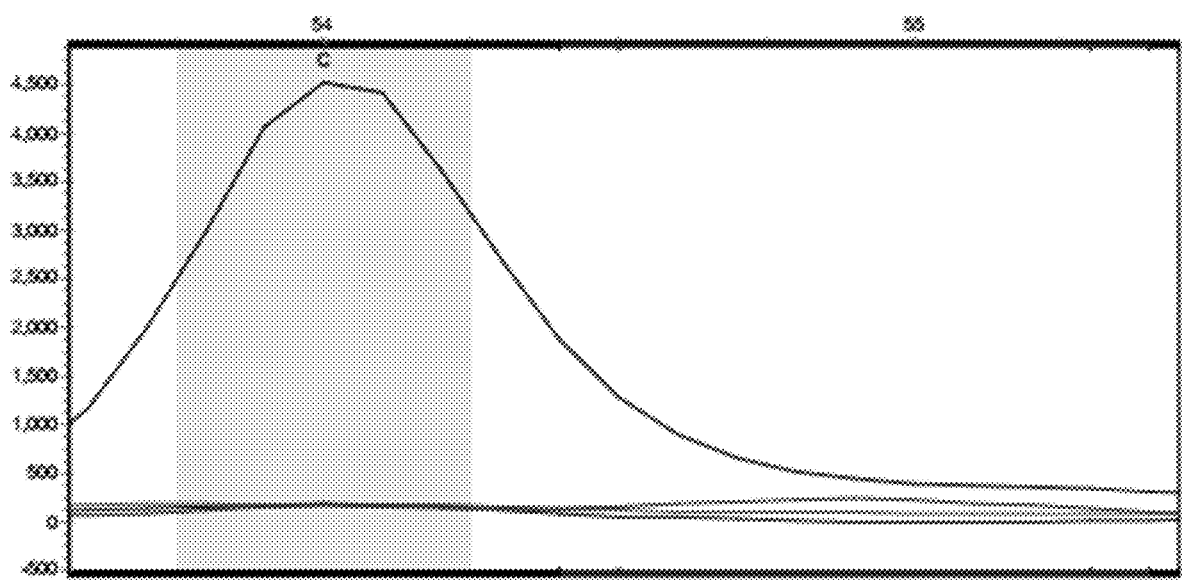
FIG. 29 shows SNAPshot sequencing results of genotype of the sample 2-97 at the site Scaffold115: 803980 (reverse compliment).
Figure 30:
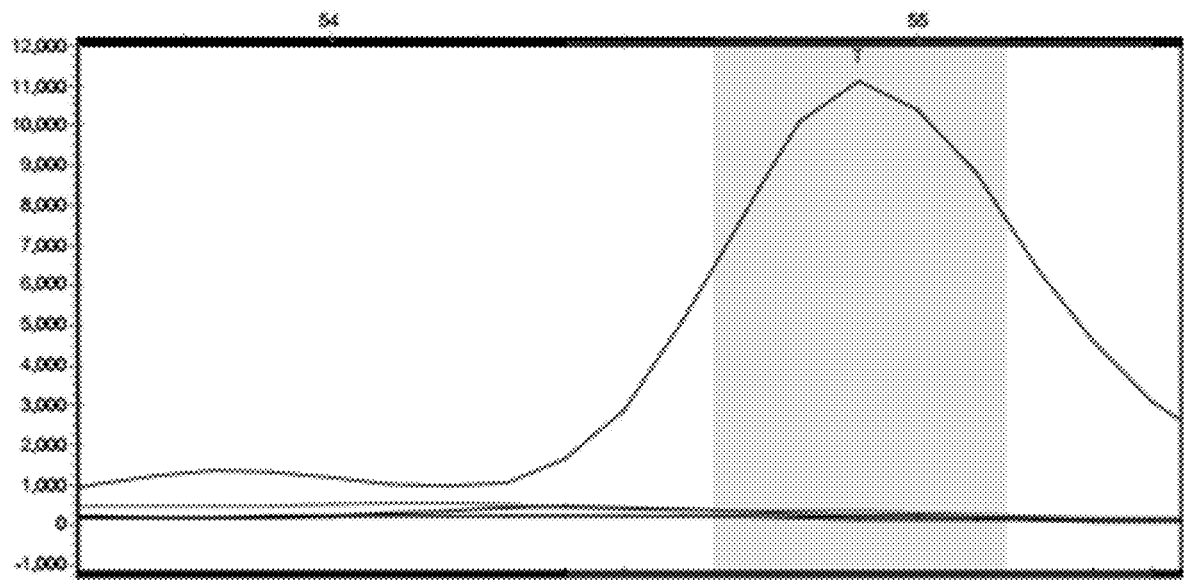
FIG. 30 shows SNAPshot sequencing results of genotype of the sample 2-94 at the site Scaffold115: 803980 (reverse compliment).
Figure 31:
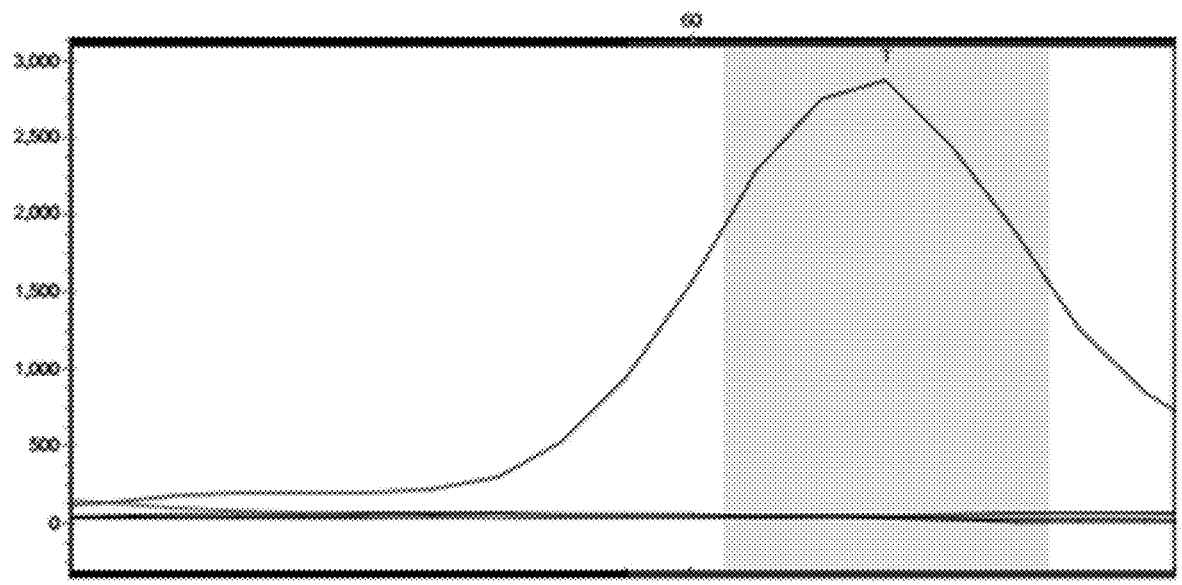
FIG. 31 shows SNAPshot sequencing results of genotype of the sample 2-93 at the site Scaffold920: 281727 (reverse compliment).
Figure 32:
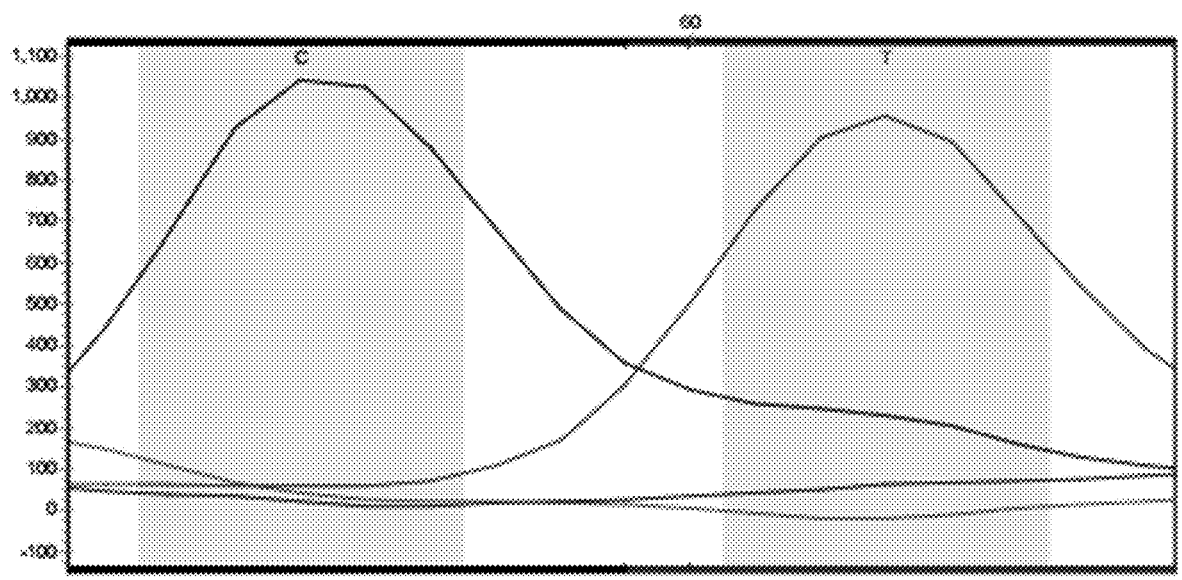
FIG. 32 shows SNAPshot sequencing results of genotype of the sample 2-94 at the site Scaffold920: 281727 (reverse compliment).
Figure 33:
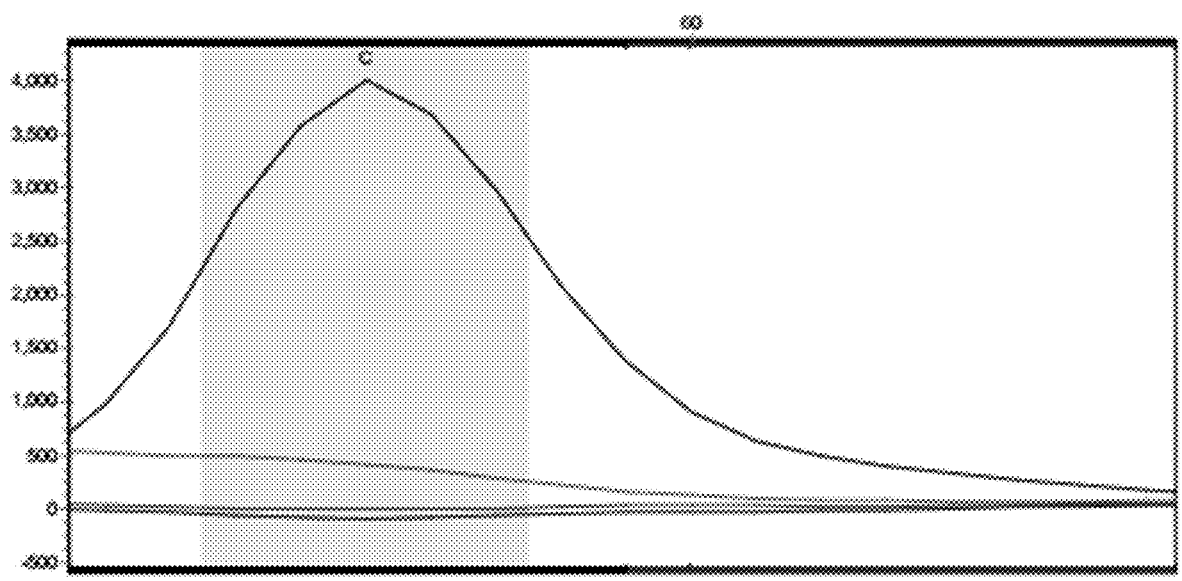
FIG. 33 shows SNAPshot sequencing results of genotype of the sample 2-98 at the site Scaffold920: 281727 (reverse compliment).
Figure 34:
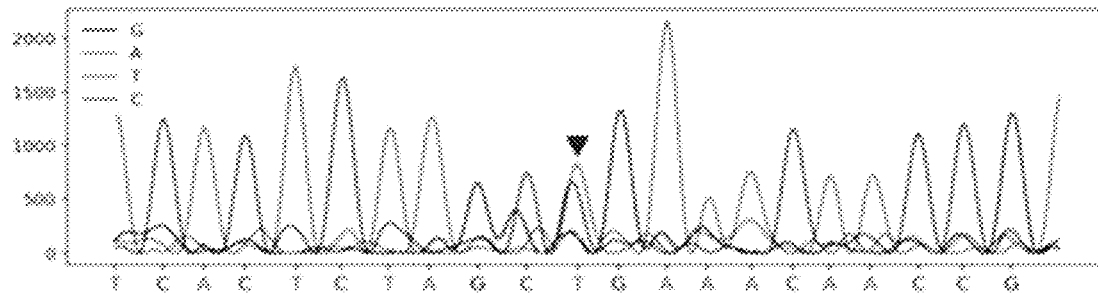
FIG. 34 shows sequencing results of genotype at the site Scaffold4239:309117 (SEQ ID NO: 41: TCACTCTAGCT-GAAACAACCG).
Figure 35:
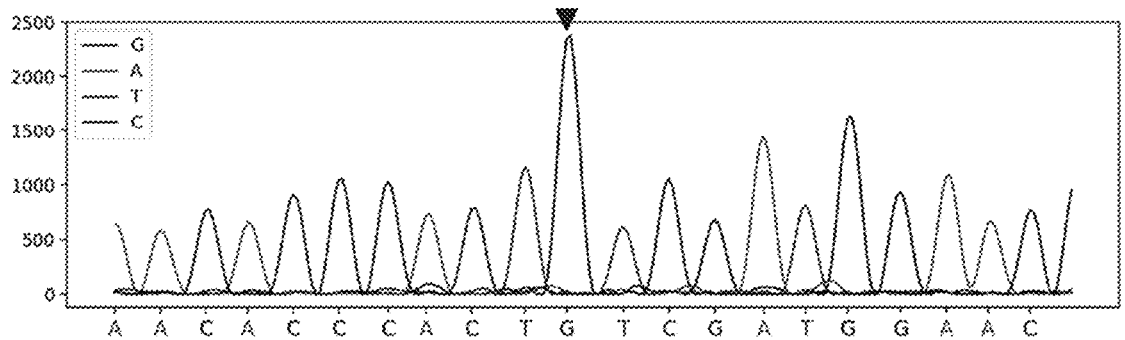
FIG. 35 shows sequencing results of genotype at the site Scaffold1989: 2316385 (SEQ ID NO: 42: AACACC-CACTGTCGATGGAAC).
Figure 38:
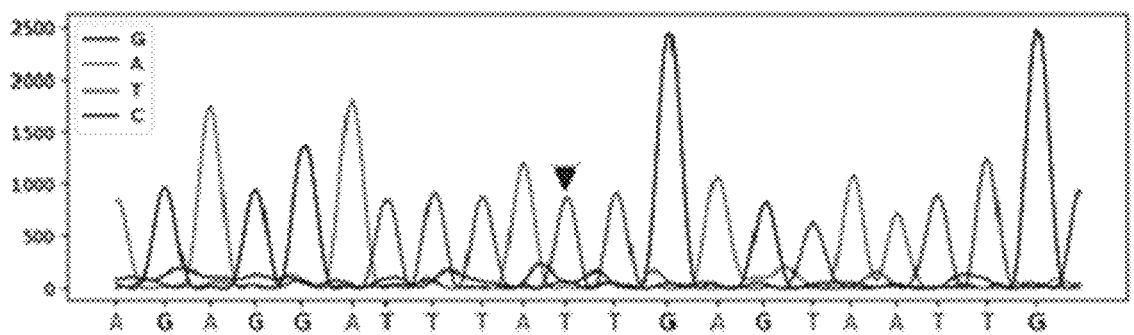
FIG. 38 shows sequencing results of genotype at the site Scaffold920: 281727 (SEQ ID NO: 45: AGAGGATTTAT-TGAGTAATTG).

The present invention will be further described in detail below with reference to the accompanying drawings and specific embodiments, and the embodiments are only used to explain the present invention, and are not used to limit the scope of the present invention. The test methods used in the following embodiments are all conventional methods unless otherwise specified. The materials and agents used, unless otherwise specified, are the agents and materials available from commercial sources.

Embodiment 1

I. Experiment Sample 191 tea plant materials located in Guangdong Province Tea Plant Germplasm Resource Bank (Yingde, Guangdong, 113.30E, 24.3ON) were collected, including 124 from Guangdong, 20 from Fujian, 14 from Guangxi, 9 from Zhejiang, 6 from Hunan, 6 from Yunnan, 1 from Jiangxi, 1 from Guizhou, 1 from Taiwan, and 8 offspring of Kenyan tea, 1 offspring of Georgian species. The selected materials are widely representative.

The selected resources are randomly distributed in the resource bank. Double row per plant was used, each row is 4 m, the row spacing is 1.5 m, and the plant spacing is 35 cm. The resource bank was subjected to conventional water and fertilizer management. At the end of 2016, the resources were pruned and deep pits were applied with base fertilizer, 4 tons of organic fertilizer, 0.75 tons of peanut bran and 5 kg of compound fertilizer per acre. After picking spring tea and summer tea in 2017, pruning and topdressing outside the root were conducted, 15 kg compound fertilizer and 30 kg urea per acre. On Mar. 15, 2017, Jun. 25, 2017, and Sep. 28, 2017, the new shoots (one bud with two leaves) of the tea plant were picked, to make steamed green samples, and tea soup was prepared according to water extraction method.

II. Phenotypic Data Analysis

1. Experimental Procedure

The high-performance liquid chromatography was used to detect (+)-catechin in tea soup related to the taste of tea plant, referring to the Chinese standard detection method.

2. Experimental Results (+)-Catechin content is shown in Table 1.

TABLE 1

Percentage of CAF in dry matter from different tea plant resources in different seasons

| Sample | (+)-Catechin content (%) | | |
|---|---|---|---|
| | Spring | Summer | Autumn |
| Sample 1 | 1.05 | 1.09 | 1.22 |
| Sample 2 | 1.17 | 1.06 | 1.13 |
| Sample 3 | 1.10 | 1.43 | 1.45 |
| Sample 4 | 1.01 | 1.24 | 1.07 |
| Sample 5 | 0.93 | 1.00 | 0.99 |
| Sample 6 | 1.19 | 1.59 | 1.34 |
| Sample 7 | 1.02 | 1.26 | 1.29 |
| Sample 8 | 1.01 | 1.24 | 1.33 |
| Sample 9 | 1.01 | 1.08 | 1.15 |
| Sample 10 | 0.96 | 1.07 | 1.16 |
| Sample 11 | 1.21 | 1.46 | 1.51 |
| Sample 12 | 0.99 | 1.18 | 1.08 |
| Sample 13 | 0.95 | 1.09 | 1.14 |
| Sample 14 | 0.89 | 1.21 | 1.39 |
| Sample 15 | 1.10 | 1.13 | 1.14 |
| Sample 16 | 1.03 | 1.02 | 1.11 |
| Sample 17 | 1.09 | 1.05 | 1.39 |
| Sample 18 | 1.35 | 1.28 | 1.46 |
| Sample 19 | 0.97 | 0.90 | 1.01 |
| Sample 20 | 1.20 | 1.19 | 1.08 |
| Sample 21 | 0.98 | 0.96 | 0.97 |
| Sample 22 | 1.41 | 1.31 | 1.46 |
| Sample 23 | 1.17 | 1.13 | 1.31 |
| Sample 24 | 1.29 | 1.54 | 1.38 |
| Sample 25 | 1.19 | 1.16 | 1.16 |
| Sample 26 | 0.98 | 1.18 | 0.96 |
| Sample 27 | 1.04 | 1.05 | 1.17 |
| Sample 28 | 0.97 | 1.07 | 1.12 |
| Sample 29 | 3.04 | 2.94 | 3.38 |
| Sample 30 | 1.19 | 1.32 | 1.49 |
| Sample 31 | 0.93 | 0.96 | 1.07 |
| Sample 32 | 1.05 | 1.03 | 1.20 |
| Sample 33 | 1.01 | 1.09 | 1.06 |
| Sample 34 | 1.31 | 1.44 | 1.46 |
| Sample 35 | 1.05 | 1.21 | 1.10 |
| Sample 36 | 1.03 | 1.20 | 1.12 |
| Sample 37 | 0.93 | 0.95 | 1.24 |
| Sample 38 | 1.00 | 0.96 | 1.12 |
| Sample 39 | 1.02 | 1.11 | 1.22 |
| Sample 40 | 1.05 | 1.27 | 1.82 |
| Sample 41 | 1.36 | 1.59 | 1.47 |
| Sample 42 | 2.15 | 2.23 | 1.28 |
| Sample 43 | 1.84 | 2.51 | 2.15 |
| Sample 44 | 1.10 | 1.32 | 1.08 |
| Sample 45 | 1.14 | 1.12 | 1.04 |
| Sample 46 | 1.26 | 1.30 | 1.65 |
| Sample 47 | 1.29 | 1.10 | 1.16 |
| Sample 48 | 1.09 | 1.19 | 1.17 |
| Sample 49 | 1.58 | 1.76 | 1.69 |
| Sample 50 | 0.93 | 1.14 | 1.07 |
| Sample 51 | 1.00 | 1.09 | 1.18 |
| Sample 52 | 1.00 | 1.03 | 1.31 |
| Sample 53 | 0.98 | 1.18 | 1.12 |
| Sample 54 | 0.92 | 1.21 | 1.00 |
| Sample 55 | 0.94 | 0.92 | 0.99 |
| Sample 56 | 0.94 | 0.99 | 1.16 |
| Sample 57 | 0.84 | 0.97 | 1.05 |
| Sample 58 | 0.91 | 0.94 | 1.07 |
| Sample 59 | 1.00 | 1.21 | 1.23 |
| Sample 60 | 1.02 | 1.06 | 1.18 |
| Sample 61 | 1.31 | 1.91 | 1.76 |
| Sample 62 | 1.03 | 1.17 | 1.30 |
| Sample 63 | 0.92 | 0.90 | 0.93 |
| Sample 64 | 0.93 | 0.99 | 1.15 |
| Sample 65 | 0.98 | 1.24 | 1.42 |
| Sample 66 | 1.36 | 1.44 | 1.15 |
| Sample 67 | 1.22 | 0.94 | 1.37 |
| Sample 68 | 0.98 | 1.00 | 1.11 |
| Sample 69 | 0.91 | 0.92 | 1.05 |
| Sample 70 | 1.05 | 1.33 | 1.32 |
| Sample 71 | 0.99 | 0.99 | 1.12 |
| Sample 72 | 1.35 | 1.74 | 1.87 |
| Sample 73 | 0.93 | 0.94 | 1.03 |
| Sample 74 | 0.89 | 1.09 | 1.04 |
| Sample 75 | 1.33 | 1.17 | 1.35 |
| Sample 76 | 1.33 | 1.57 | 1.80 |
| Sample 77 | 1.04 | 1.15 | 1.04 |
| Sample 78 | 2.79 | 2.92 | 2.99 |
| Sample 79 | 2.65 | 2.69 | 2.78 |
| Sample 80 | 0.96 | 0.91 | 1.07 |
| Sample 81 | 2.53 | 3.14 | 2.88 |
| Sample 82 | 1.15 | 1.21 | 1.15 |
| Sample 83 | 1.16 | 1.10 | 1.16 |
| Sample 84 | 1.81 | 1.37 | 1.82 |
| Sample 85 | 1.01 | 1.21 | 1.70 |
| Sample 86 | 1.65 | 1.95 | 1.73 |
| Sample 87 | 1.54 | 1.62 | 1.44 |
| Sample 88 | 1.13 | 1.13 | 1.23 |
| Sample 89 | 0.94 | 0.97 | 1.18 |
| Sample 90 | 1.00 | 0.98 | 1.04 |
| Sample 91 | 1.10 | 1.20 | 1.24 |
| Sample 92 | 1.10 | 1.15 | 1.18 |
| Sample 93 | 1.15 | 1.75 | 1.25 |
| Sample 94 | 1.14 | 1.22 | 1.21 |
| Sample 95 | 1.02 | 1.16 | 1.23 |
| Sample 96 | 1.16 | 1.20 | 1.23 |

TABLE 1-continued

Percentage of CAF in dry matter from different tea plant resources in different seasons

| Sample | (+)-Catechin content (%) | | |
|---|---|---|---|
| | Spring | Summer | Autumn |
| Sample 97 | 1.24 | 1.06 | 1.00 |
| Sample 98 | 1.31 | 1.69 | 1.76 |
| Sample 99 | 1.02 | 1.18 | 1.04 |
| Sample 100 | 0.92 | 1.01 | 0.96 |
| Sample 101 | 1.11 | 1.06 | 1.21 |
| Sample 102 | 1.08 | 1.20 | 1.32 |
| Sample 103 | 0.83 | 0.98 | 1.16 |
| Sample 104 | 1.02 | 1.09 | 0.99 |
| Sample 105 | 1.28 | 1.17 | 1.12 |
| Sample 106 | 1.16 | 1.17 | 1.13 |
| Sample 107 | 1.09 | 1.23 | 1.31 |
| Sample 108 | 2.16 | 1.59 | 2.07 |
| Sample 109 | 1.08 | 1.12 | 1.44 |
| Sample 110 | 1.11 | 1.22 | 1.53 |
| Sample 111 | 1.04 | 1.04 | 1.15 |
| Sample 112 | 0.89 | 1.19 | 1.19 |
| Sample 113 | 1.08 | 1.04 | 1.24 |
| Sample 114 | 1.05 | 1.20 | 1.42 |
| Sample 115 | 1.58 | 1.09 | 1.25 |
| Sample 116 | 1.08 | 1.09 | 1.35 |
| Sample 117 | 1.06 | 1.17 | 1.43 |
| Sample 118 | 1.39 | 1.23 | 1.66 |
| Sample 119 | 1.10 | 1.06 | 1.19 |
| Sample 120 | 1.61 | 1.68 | 1.65 |
| Sample 121 | 1.18 | 1.19 | 1.29 |
| Sample 122 | 2.30 | 2.38 | 2.47 |
| Sample 123 | 1.16 | 1.30 | 1.24 |
| Sample 124 | 1.07 | 1.16 | 1.17 |
| Sample 125 | 1.07 | 1.16 | 1.18 |
| Sample 126 | 1.29 | 1.47 | 1.83 |
| Sample 127 | 1.12 | 1.02 | 1.32 |
| Sample 128 | 1.08 | 2.21 | 1.64 |
| Sample 129 | 1.15 | 1.41 | 1.49 |
| Sample 130 | 0.99 | 0.98 | 1.13 |
| Sample 131 | 1.21 | 1.41 | 1.38 |
| Sample 132 | 0.92 | 0.92 | 1.00 |
| Sample 133 | 1.13 | 1.23 | 1.26 |
| Sample 134 | 1.00 | 1.06 | 1.15 |
| Sample 135 | 0.96 | 1.23 | 2.12 |
| Sample 136 | 2.02 | 1.81 | 1.37 |
| Sample 137 | 2.85 | 3.03 | 2.89 |
| Sample 138 | 1.01 | 1.50 | 1.55 |
| Sample 139 | 2.55 | 2.84 | 2.82 |
| Sample 140 | 0.89 | 1.18 | 1.32 |
| Sample 141 | 0.90 | 1.18 | 1.13 |
| Sample 142 | 1.20 | 1.18 | 1.31 |
| Sample 143 | 1.02 | 1.14 | 1.27 |
| Sample 144 | 0.90 | 1.02 | 1.08 |
| Sample 145 | 1.31 | 1.16 | 1.38 |
| Sample 146 | 1.29 | 1.41 | 1.31 |
| Sample 147 | 1.21 | 1.16 | 1.12 |
| Sample 148 | 1.37 | 1.30 | 1.21 |
| Sample 149 | 0.91 | 1.30 | 2.99 |
| Sample 150 | 1.10 | 1.29 | 1.68 |
| Sample 151 | 0.95 | 1.27 | 1.28 |
| Sample 152 | 0.92 | 1.16 | 1.98 |
| Sample 153 | 0.97 | 1.00 | 1.01 |
| Sample 154 | 0.93 | 0.92 | 1.06 |
| Sample 155 | 1.25 | 1.24 | 1.27 |
| Sample 156 | 1.45 | 1.84 | 1.44 |
| Sample 157 | 1.57 | 1.48 | 1.61 |
| Sample 158 | 1.08 | 1.20 | 1.25 |
| Sample 159 | 1.11 | 1.20 | 1.17 |
| Sample 160 | 1.37 | 1.42 | 1.13 |
| Sample 161 | 0.89 | 1.17 | 1.31 |
| Sample 162 | 0.93 | 1.00 | 1.46 |
| Sample 163 | 0.99 | 1.14 | 1.20 |
| Sample 164 | 1.21 | 1.03 | 1.10 |
| Sample 165 | 1.24 | 1.45 | 1.61 |
| Sample 166 | 0.97 | 1.20 | 1.39 |
| Sample 167 | 0.95 | 0.92 | 0.96 |
| Sample 168 | 1.07 | 1.08 | 1.01 |
| Sample 169 | 1.10 | 1.31 | 1.34 |
| Sample 170 | 0.87 | 1.28 | 1.10 |
| Sample 171 | 0.94 | 0.94 | 1.01 |
| Sample 172 | 0.85 | 1.19 | 1.24 |
| Sample 173 | 1.58 | 1.68 | 1.55 |
| Sample 174 | 0.97 | 0.87 | 0.97 |
| Sample 175 | 0.97 | 1.01 | 1.12 |
| Sample 176 | 1.61 | 0.94 | 1.24 |
| Sample 177 | 1.42 | 1.37 | 1.44 |
| Sample 178 | 1.06 | 1.31 | 0.88 |
| Sample 179 | 2.80 | 2.73 | 1.25 |
| Sample 180 | 1.09 | 1.03 | 1.30 |
| Sample 181 | 1.02 | 1.05 | 1.16 |
| Sample 182 | 1.11 | 1.28 | 1.25 |
| Sample 183 | 1.02 | 1.00 | 1.16 |
| Sample 184 | 1.48 | 1.22 | 1.17 |
| Sample 185 | 1.13 | 1.30 | 1.25 |
| Sample 186 | 1.22 | 1.15 | 1.09 |
| Sample 187 | 1.38 | 1.32 | 1.42 |
| Sample 188 | 4.01 | 2.98 | 1.38 |
| Sample 189 | 1.42 | 1.21 | 0.98 |
| Sample 190 | 0.96 | 0.96 | 1.17 |
| Sample 191 | 2.79 | 2.82 | 3.95 |

The variation of (+)-catechin content in the population is shown in Table 2 and FIG. 1.

TABLE 2

Phenotypic variation in (+)-catechin traits

| Season | Range (%) | Mean (%) | Standard deviation $^a$SD | Coefficient of variation $^b$CV | Diversity index $^c$H' | Heritability |
|---|---|---|---|---|---|---|
| Spring | 0.83~4.01 | 1.22 | 0.45 | 0.37 | 1.49 | 0.90 |
| Summer | 0.87~3.14 | 1.3 | 0.44 | 0.34 | 1.51 | |
| Autumn | 0.88~3.95 | 1.36 | 0.44 | 0.32 | 1.58 | |

III. Association Analysis Between Genotype and Traits

1. Experimental Procedure

The CTAB method was used to extract total DNA from buds of 191 tea plant resources, and it was ensured that A260/A280 of each DNA sample is between 1.8 and 2.0, and the concentration was greater than 100 μg/μl. The extracted DNA samples were used to detect genotypes located in the SNP site 1 (Scaffold4239:309117), the SNP site 2 (Scaffold3614: 66549), the SNP site 3 (Scaffold349: 3413816), the SNP site 4 (Scaffold1989: 2316385), the SNP site 5 (Scaffold451: 940283), the SNP site 6 (Scaffold3727: 442660), the SNP site 7 (Scaffold115:803980), and the SNP site 8 (Scaffold920:281727) of the "Shuchazao" CSS cultivar tea plant genome (http://tpia.teaplant.org/index.html), respectively. The association analysis of traits and markers was performed, significance level of the association was judged by P-value, and the p-value less than 1.25E−05 was the significance level.

2. Experimental Results

The p-values of the eight SNP sites in different seasons are shown in Table 3.

TABLE 3 p-values of eight SNP sites in different seasons

| | Season | | |
|---|---|---|---|
| | Spring | Summer | Autumn |
| Scaffold4239: 309117 | 2.03E−08 | 5.94E−08 | 1.48E−07 |
| Scaffold3614: 66549 | 3.75E−16 | 2.98E−19 | 5.46E−15 |
| Scaffold349: 3413816 | 3.54E−13 | 5.96E−15 | 2.43E−13 |
| Scaffold1989: 2316385 | 2.67E−15 | 1.68E−19 | 1.80E−15 |
| Scaffold451: 940283 | 3.14E−06 | 2.42E−06 | 2.19E−06 |
| Scaffold3727: 442660 | 5.49E−07 | 3.18E−08 | 4.49E−07 |
| Scaffold115: 803980 | 1.23E−13 | 9.83E−14 | 1.83E−10 |
| Scaffold920: 281727 | 8.97E−21 | 3.13E−21 | 8.26E−12 |

Embodiment 2 Verification of SNP Site

I. Experimental Method

Genotypes of the SNP site 1 (Scaffold4239:309117), the SNP site 2 (Scaffold3614: 66549), the SNP site 3 (Scaffold349: 3413816), the SNP site 4 (Scaffold1989: 2316385), the SNP site 5 (Scaffold451: 940283), the SNP site 6 (Scaffold3727:442660), the SNP site 7 (Scaffold115: 803980), and the SNP site 8 (Scaffold920:281727) were subjected to verification in another population of 98 germplasms.

1. (+)-Catechin content of each sample was detected. The specific detection method is the same as that of Embodiment 1.
2. SnapShot technology platform was used to detect the genotypes of the SNP site 1 (Scaffold4239:309117), the SNP site 2 (Scaffold3614: 66549), the SNP site 3 (Scaffold349: 3413816), the SNP site 4 (Scaffold1989: 2316385), the SNP site 5 (Scaffold451: 940283), the SNP site 6 (Scaffold3727: 442660), the SNP site 7 (Scaffold115:803980), and the SNP site 8 (Scaffold920:281727).

This method designed primers of different lengths for different mutation sites, after SNAPshot reaction, the products were analyzed by electrophoresis, five-color fluorescence detection, and Gene mapper analysis, and multiple SNP sites can be detected in one sequencing reaction. SNAPshot was used for site-specific sequence analysis, and the basic principle thereof followed the dideoxy termination method in direct DNA sequencing, except that only ddNTPs with different fluorescent labels were used in the PCR reaction. Since the 3'-end of the primers of each SNP site is close to the SNP point, each of the primers was extended by only one nucleotide according to the sequence of the template under the action of the polymerase. Then an advanced fluorescence detection system was used to detect the type of that nucleotide that is extended.

(1) Design of Primers

Primers were designed and synthesized according to the position of Scaffold4239:309117. In particular, Scaffold4239:309117 each extended 500 bp upstream and downstream. A nucleotide sequence thereof is shown as SEQ ID NO: 1 (FIG. 2, wherein N denotes the base to be tested at Scaffold4239:309117).

PCR primers:

F:
    (SEQ ID NO: 2)
GAAGACTAACCCGTATCGAG;

R:
    (SEQ ID NO: 3)
ACACTTACAGTCTCTTGCGG.

Single base extension primer:

(SEQ ID NO: 33)
ctgactgactgactgactgactATTGTCTCGTTGCTTCGGTTGTTTC.

Primers were designed and synthesized according to the position of Scaffold3614: 66549. In particular, Scaffold3614: 66549 each extended 500 bp upstream and downstream. A nucleotide sequence thereof is shown as SEQ ID NO: 5 (FIG. 3, wherein N denotes the base to be tested at Scaffold3614: 66549).

PCR primers:

F:
    (SEQ ID NO: 5)
GATGACACAACCCTCATCTG;

R:
    (SEQ ID NO: 6)
AATGTATGCCCGGTAAGGAC.

Single base extension primer:

(SEQ ID NO: 34)
gactACTAACTTTACGCCCACGACCCA.

Primers were designed and synthesized according to the position of Scaffold349: 3413816. In particular, Scaffold349: 3413816 each extended 500 bp upstream and downstream. A nucleotide sequence thereof is shown as SEQ ID NO: 7 (FIG. 4, wherein N denotes the base to be tested at Scaffold349: 3413816).

PCR primers:

primer F:
(SEQ ID NO: 8)
TCTCTGCACTGTTGTCACTC;

primer R:
(SEQ ID NO: 9)
CACCACACTTTCTTAGAAGG.

Single base extension primer:

(SEQ ID NO: 35)
actgactgactaAGGATCTAGTCCCTGCATAAATAACA.

Primers were designed and synthesized according to the position of Scaffold1989: 2316385. In particular, Scaffold1989: 2316385 each extended 500 bp upstream and downstream. A nucleotide sequence thereof is shown as SEQ ID NO: 10 (FIG. 5, wherein N denotes the base to be tested at Scaffold1989: 2316385).

PCR primers:

primer F:
(SEQ ID NO: 11)
GATTTGACCTTCAACGTGGG;

primer R:
(SEQ ID NO: 12)
TGCAGCGTTTGTGTTTGCAG.

Single base extension primer:

(SEQ ID NO: 36)
CTGCTGCCACCACCAACACCCACT.

Primers were designed and synthesized according to the position of Scaffold451: 940283. In particular, Scaffold451: 940283 each extended 500 bp upstream and downstream. A nucleotide sequence thereof is shown as SEQ ID NO: 13 (FIG. 6, wherein N denotes the base to be tested at Scaffold451: 940283).

PCR primers:

F:
(SEQ ID NO: 14)
GTAATAGACGGTGCAAACCC;

R:
(SEQ ID NO: 15)
CAAAGTATTTGGGAGCGCTG.

Single base extension primer:

(SEQ ID NO: 37)
actgactGTTTAAAGAACACGGGAAGCTTAC.

Primers were designed and synthesized according to the position of Scaffold3727:442660. In particular, Scaffold3727:442660 each extended 500 bp upstream and downstream. A nucleotide sequence thereof is shown as SEQ ID NO: 16 (FIG. 7, wherein N denotes the base to be tested at Scaffold3727:442660).

PCR primers:

F:
(SEQ ID NO: 17)
TTGTCCGTGTCCAATCCTTG;

R:
(SEQ ID NO: 16)
ATTGACCACCTGGAAGAAGC.

Single base extension primer:

(SEQ ID NO: 38)
ataaTCTAAGAGCAACCACCATAGCCCA.

Primers were designed and synthesized according to the position of Scaffold115: 803980. In particular, Scaffold115: 803980 each extended 500 bp upstream and downstream. A nucleotide sequence thereof is shown as SEQ ID NO: 19 (FIG. 8, wherein N denotes the base to be tested at Scaffold115: 803980).

PCR primers:

F:
(SEQ ID NO: 20)
CTTCATCTCCACCACACTTC;

R:
(SEQ ID NO: 21)
GCCCAAAGTAGCAAAGAGAG.

Single base extension primer:

(SEQ ID NO: 39)
gactgactgactgactgactgactcaGCAGAGCTTGGCAAAGAGGGATG.

Primers were designed and synthesized according to the position of Scaffold920: 281727. In particular, Scaffold920: 281727 each extended 500 bp upstream and downstream. A nucleotide sequence thereof is shown as SEQ ID NO: 22 (FIG. 9, wherein N denotes the base to be tested at Scaffold920: 281727).

PCR primers:

primer F:
(SEQ ID NO: 23)
TTCGCATTCGTCCTTTTGGG;

primer R:
(SEQ ID NO: 24)
ACGTGCTACATTCTCCATCC.

Single base extension primer:

(SEQ ID NO: 40)
tgactgactgactgactgactgactgactgactTAGCATCTAAGAAAGAGGATTTA.

(2) PCR Amplification

PCR system (10 μl) was as follows:

| | |
|---|---|
| 2 × Taq PCR Master Mix | 5 μl |
| PrimerMix (matching according to the amplification ratio) | 1 μl |
| DNA template | 1 μl |
| ddH$_2$O | 3 μl |

PCR amplification procedure was as follows:

| | | |
|---|---|---|
| 95° C. | 5 minutes | |
| 95° C. | 30 seconds | ×45 cycles |
| 56° C. | 30 seconds | |
| 72° C. | 30 seconds | |
| 72° C. | 2 minutes | |
| 4° C. | forever | |

(3) PCR Product Purification

Purification was performed using shrimp alkaline phosphatase purification. The main functional components of shrimp alkaline phosphatase MIX (EX-SAP) are SAP and ExoI.SAP enzyme, which can dephosphorylate residual dNTPs, and ExoI degrades the free single-chain primer. 4 μl of PCR product was taken and added with 2 μl of EX-SAP enzyme. The specific reaction system is shown as follows:

| Constituent of digestive system | Volume (μl) |
|---|---|
| ddH$_2$O | 0.75 |
| SAP (1 U/μl) | 0.5 |
| ExoI (5 U/μl) | 0.15 |
| 10 * SAP buffer | 0.6 |
| PCR product | 4 |
| Total volume | 6 |

After that, digestion and incubation were performed on a PCR instrument: 37° C. for 40 minutes, 85° C. for 5 minutes, 4° C. forever.

(4) SNAPshot Reaction

The PCR product was used as a template for SNAPshot reaction.

The SNAPshot reaction system is shown as follows:

| Reagent | Dosage (μl) |
|---|---|
| SNaPshot Mix | 0.5 |
| Pooled PCR Products | 3 |
| Pooled Primers | 1 |
| dH$_2$O | 0.5 |
| Total volume | 5 |

The SNAPshot reaction procedure is:

| | | |
|---|---|---|
| 95° C. | 2 minutes | |
| 95° C. | 10 seconds | ×40 cycles |
| 52° C. | 5 seconds | |
| 60° C. | 30 seconds | |
| 4° C. | forever | |

After that, the SNAPshot product was purified, and 2 μl of SAP mix was directly added to the SNAPshot reaction product. The specific reaction system was as follows:

| Constituent | Volume (μl) |
|---|---|
| Water | 0.9 |
| SAP(1 U/ul) | 0.5 |
| 10 * SAP buffer | 0.6 |
| Total | 2 |

The SNAPshot product digestion reaction was performed on a PCR instrument, and the reaction procedures were: 37° C. for 40 minutes, 75° C. for 15 minutes, 4° C. forever.

(5) On-Machine Detection

2 μl of the digested SNAPshot reaction product was taken and added into 8 μl of deionized formamide containing 0.4% LIZ120, denatured at 95° C. for 5 minutes, then quenched at −20° C., and then sequenced on 3730XL.

(6) Result Analysis

The .fsa results obtained by GeneMarker analysis were used to derive peak plots and table files, and to calculate the SNP mutant type of each sample.

II. Experimental Results (+)-Catechin content and genotypes of SNP1, SNP2, SNP3, SNP4, SNP5, SNP6, SNP7, SNP8 sites of each sample are shown in Table 4, and the SNAPshot sequencing results of some samples are shown in FIG. 8 to FIG. 24.

TABLE 4

The (+)-catechin content in dry matter and genotype of the resource in the population:

| Sample | (+)-Catechin content (%) | SNP1 genotype | SNP2 genotype | SNP3 genotype | SNP4 genotype | SNP5 genotype | SNP6 genotype | SNP7 genotype | SNP8 genotype |
|---|---|---|---|---|---|---|---|---|---|
| Sample 2-1 | 1.00 | GA | CT | AA | GG | CC | GA | AA | AA |
| Sample 2-2 | 0.98 | GA | CC | AA | GG | CC | GA | AA | AA |
| Sample 2-3 | 0.99 | GG | TT | AA | GG | CC | GG | AA | AA |
| Sample 2-4 | 1.08 | GG | TT | AA | GG | CC | GG | AA | AA |
| Sample 2-5 | 0.91 | GG | CT | AA | GG | CC | GG | AA | AA |
| Sample 2-6 | 1.18 | GG | TT | AA | GG | CC | GG | AA | AA |
| Sample 2-7 | 1.12 | GG | TT | AA | GG | CC | GG | AA | AA |
| Sample 2-8 | 0.88 | GG | TT | AA | GG | CC | GG | AA | AA |
| Sample 2-9 | 0.89 | GG | TT | AA | GG | CC | GG | AA | AA |

TABLE 4-continued

The (+)-catechin content in dry matter and genotype of the resource in the population:

| Sample | (+)-Catechin content (%) | SNP1 genotype | SNP2 genotype | SNP3 genotype | SNP4 genotype | SNP5 genotype | SNP6 genotype | SNP7 genotype | SNP8 genotype |
|---|---|---|---|---|---|---|---|---|---|
| Sample 2-10 | 1.07 | GG | TT | AA | GG | CC | GG | AA | AA |
| Sample 2-11 | 1.10 | AA | CT | AA | GG | CC | AA | AA | AA |
| Sample 2-12 | 0.90 | GG | TT | GA | GG | CC | GG | AA | AA |
| Sample 2-13 | 1.09 | GA | CT | AA | GG | CC | GA | AA | AA |
| Sample 2-14 | 3.44 | AA | CC | AA | GG | CC | AA | AA | AA |
| Sample 2-15 | 1.10 | GG | TT | AA | GG | CC | GG | AA | AA |
| Sample 2-16 | 0.96 | GG | TT | AA | GG | CC | GG | AA | AA |
| Sample 2-17 | 0.99 | GG | TT | AA | GG | CC | GG | AA | AA |
| Sample 2-18 | 1.07 | AA | CT | AA | GG | CC | AA | AA | AA |
| Sample 2-19 | 1.18 | GG | TT | GA | GG | CC | GG | AA | AA |
| Sample 2-20 | 1.95 | AA | CT | AA | GG | CC | AA | AA | AA |
| Sample 2-21 | 0.99 | GG | TT | AA | GG | CC | GG | AA | AA |
| Sample 2-22 | 1.00 | GG | TT | AA | GG | CC | GG | AA | Not detected |
| Sample 2-23 | 0.98 | GG | TT | AA | GG | CC | GG | AA | AA |
| Sample 2-24 | 1.12 | GA | CT | AA | GG | CC | GA | AA | AA |
| Sample 2-25 | 1.11 | GG | TT | AA | GG | CC | GG | AA | AA |
| Sample 2-26 | 1.18 | GA | CT | AA | GG | CC | GA | AA | AA |
| Sample 2-27 | 1.03 | GA | TT | AA | GG | CC | GA | GA | AA |
| Sample 2-28 | 0.96 | GG | TT | AA | GG | CC | GG | AA | Not detected |
| Sample 2-29 | 0.98 | GG | TT | AA | GG | CC | GG | AA | AA |
| Sample 2-30 | 0.98 | GG | TT | AA | GG | CC | GG | AA | AA |
| Sample 2-31 | 0.96 | GG | TT | AA | GG | CC | GG | AA | AA |
| Sample 2-32 | 1.01 | GG | TT | GA | GG | CC | GG | AA | Not detected |
| Sample 2-33 | 0.81 | GG | TT | AA | GG | CC | GG | AA | AA |
| Sample 2-34 | 1.06 | GG | TT | AA | GG | CC | GG | AA | AA |
| Sample 2-35 | 1.13 | GG | TT | AA | GG | CC | GG | AA | AA |
| Sample 2-36 | 0.92 | GG | TT | GA | GG | CC | GG | AA | AA |
| Sample 2-37 | 1.25 | GA | TT | AA | GG | CC | GA | AA | AA |
| Sample 2-38 | 0.97 | GG | CC | GA | GG | CC | GG | AA | Not detected |
| Sample 2-39 | 0.99 | GA | TT | AA | GG | CC | GA | AA | AA |
| Sample 2-40 | 0.93 | GA | TT | AA | GG | CC | GA | AA | AA |
| Sample 2-41 | 0.87 | GG | TT | AA | GG | CC | GG | AA | AA |
| Sample 2-42 | 0.99 | GG | TT | AA | GG | CC | GG | AA | AA |
| Sample 2-43 | 1.16 | GA | TT | AA | GG | CC | GA | AA | AA |
| Sample 2-44 | 1.18 | AA | CT | AA | GG | CC | AA | AA | AA |
| Sample 2-45 | 1.20 | GG | TT | GA | GG | CC | GG | AA | Not detected |
| Sample 2-46 | 1.01 | GA | TT | AA | GG | CC | GA | GA | AA |
| Sample 2-47 | 0.92 | GG | TT | AA | GG | CC | GG | AA | AA |
| Sample 2-48 | 0.96 | GG | TT | AA | GG | CC | GG | AA | Not detected |
| Sample 2-49 | 1.02 | GG | TT | GA | GG | CC | GG | AA | AA |
| Sample 2-50 | 0.97 | GG | TT | AA | GG | CC | GG | GA | AA |
| Sample 2-51 | 0.89 | GA | TT | AA | GG | CC | GA | AA | AA |
| Sample 2-52 | 1.13 | GG | TT | AA | GG | CC | GG | AA | AA |
| Sample 2-53 | 1.21 | GG | TT | AA | GG | CC | GG | AA | AA |
| Sample 2-54 | 1.12 | GG | TT | AA | GG | CC | GG | AA | AA |
| Sample 2-55 | 1.11 | GG | TT | AA | GG | CC | GG | AA | AA |
| Sample 2-56 | 1.02 | GG | TT | AA | GG | CC | GG | AA | AA |
| Sample 2-57 | 0.99 | GG | TT | AA | GA | CC | GG | AA | AA |
| Sample 2-58 | 1.03 | GG | TT | AA | GG | CC | GG | AA | AA |
| Sample 2-59 | 1.14 | GG | TT | AA | GG | CC | GG | AA | AA |
| Sample 2-60 | 1.04 | GG | TT | AA | GG | CC | GG | AA | AA |
| Sample 2-61 | 0.97 | GG | TT | AA | GG | CC | GG | AA | AA |
| Sample 2-62 | 1.09 | GG | TT | AA | GG | CC | GG | AA | AA |
| Sample 2-63 | 1.45 | AA | TT | AA | GG | CC | AA | AA | AA |
| Sample 2-64 | 0.96 | GG | TT | AA | GA | CC | GG | AA | AA |
| Sample 2-65 | 1.09 | GG | TT | AA | GG | CC | GG | AA | Not detected |
| Sample 2-66 | 1.24 | GG | TT | GG | GG | CC | GG | AA | AA |
| Sample 2-67 | 1.05 | GG | TT | AA | GG | CC | GG | AA | AA |
| Sample 2-68 | 0.89 | GG | TT | GA | GG | CC | GG | AA | AA |
| Sample 2-69 | 0.97 | GG | CT | AA | GA | CC | GG | AA | AA |
| Sample 2-70 | 1.05 | GG | TT | AA | GG | CC | GG | AA | Not detected |
| Sample 2-71 | 1.09 | GG | TT | AA | GG | CC | GG | AA | AA |
| Sample 2-72 | 0.95 | GA | CT | AA | GG | CC | GA | AA | AA |
| Sample 2-73 | 1.10 | GA | CT | AA | GG | CC | GA | AA | AA |
| Sample 2-74 | 1.13 | GG | TT | AA | GG | CC | GG | AA | Not detected |
| Sample 2-75 | 1.25 | AA | CT | AA | GG | CC | AA | AA | AA |
| Sample 2-76 | 1.04 | GG | TT | AA | GG | CC | GG | AA | AA |
| Sample 2-77 | 0.97 | GA | CC | GG | AA | CT | GA | GA | GG |
| Sample 2-78 | 0.88 | GG | TT | AA | GA | CC | GG | AA | AA |
| Sample 2-79 | 1.28 | GG | TT | AA | GG | CC | GG | AA | AA |
| Sample 2-80 | 0.89 | GA | TT | AA | GG | CC | GA | GA | AA |
| Sample 2-81 | 0.92 | GG | TT | AA | GG | CC | GG | AA | AA |
| Sample 2-82 | 1.01 | GG | TT | AA | GG | CC | GG | AA | AA |
| Sample 2-83 | 1.08 | GA | TT | AA | GG | CC | GA | AA | AA |
| Sample 2-84 | 1.24 | GG | TT | AA | GG | CC | GG | AA | AA |

TABLE 4-continued

The (+)-catechin content in dry matter and genotype of the resource in the population:

| Sample | (+)-Catechin content (%) | SNP1 genotype | SNP2 genotype | SNP3 genotype | SNP4 genotype | SNP5 genotype | SNP6 genotype | SNP7 genotype | SNP8 genotype |
|---|---|---|---|---|---|---|---|---|---|
| Sample 2-85 | 0.97 | GG | CT | AA | GG | CC | GG | AA | AA |
| Sample 2-86 | 0.98 | GA | TT | AA | GG | CC | GA | AA | AA |
| Sample 2-87 | 1.03 | GA | TT | AA | GG | CC | GA | AA | AA |
| Sample 2-88 | 1.15 | GA | TT | AA | GG | CC | GA | AA | AA |
| Sample 2-89 | 0.98 | GA | TT | AA | GG | CC | GA | AA | AA |
| Sample 2-90 | 0.86 | GG | TT | AA | GG | CC | GG | AA | AA |
| Sample 2-91 | 0.93 | GG | TT | AA | GG | CC | GG | AA | AA |
| Sample 2-92 | 1.07 | GG | TT | AA | GG | CC | GG | AA | Not detected |
| Sample 2-93 | 1.13 | GG | TT | AA | GG | CC | GG | AA | AA |
| Sample 2-94 | 0.89 | GG | CT | AA | GG | CC | GG | AA | GA |
| Sample 2-95 | 1.04 | GG | CT | GA | GG | CC | GG | AA | AA |
| Sample 2-96 | 1.09 | GG | TT | AA | GG | CC | GG | AA | AA |
| Sample 2-97 | 4.02 | AA | CC | GG | AA | TT | AA | GG | GG |
| Sample 2-98 | 2.16 | AA | CC | GG | AA | CT | AA | GA | GG |

The significance analysis results show that the genotype of Scaffold4239:309117 is extremely significantly correlated with (+)-catechin content, the correlation coefficient is 0.7, p-value is $8.79 \times 10^{-16}$, F-value (6.91/3.94) is 92.9, which is a recessive mutation, and the (+)-catechin content in the dry matter of tea soup corresponding to an AA genotype sample has extremely significant difference compared with GG and GA genotype samples. It is statistically judged that, when the genotype of the sample is double mutant AA, the (+)-catechin content in the dry matter in the tea plant is more likely to be higher than the normal average of the sample of which the genotype is wild type GG or single mutant GA.

The significance analysis results show that, the genotype of Scaffold3614: 66549 is extremely significantly correlated with (+)-catechin content, the correlation coefficient is 0.59, p-value is $1.24 \times 10^{-10}$, F-value (6.91/3.94) is 52.1, which is a recessive mutation, the (+)-catechin content in the dry matter corresponding to a CC genotype sample has extremely significant difference compared with TT and CT genotype samples. It is statistically judged that, when the genotype of the sample is double mutant CC, the (+)-catechin content in the dry matter in the tea plant is more likely to be higher than the sample of which the genotype is wild type TT or single mutant CT.

The significance analysis results show that, the genotype of Scaffold349: 3413816 is extremely significantly correlated with (+)-catechin content, the correlation coefficient is 0.48, p-value is $4.78 \times 10^{-7}$, F-value (6.91/3.94) is 29.2, which is a recessive mutation, the (+)-catechin content in the dry matter of tea soup corresponding to a GG genotype sample has extremely significant difference compared with GA and AA genotype samples. It is statistically judged that, when the genotype of the sample is double mutant GG, the (+)-catechin content in the dry matter in the tea plant is more likely to be higher than the sample of which the genotype is wild type AA or single mutant GA.

The significance analysis results show that, the genotype of Scaffold1989: 2316385 is extremely significantly correlated with (+)-catechin content, the correlation coefficient is 0.45, p-value is $3.16 \times 10^{-6}$, F-value (6.91/3.94) is 18.7, which is a recessive mutation, the (+)-catechin content in the dry matter of tea soup corresponding to an AA genotype sample has extremely significant difference compared with GA and GG genotype samples. It is statistically judged that, when the genotype of the sample is double mutant AA, the (+)-catechin content in the dry matter in the tea plant is more likely to be higher than the normal average of the sample of which the genotype is wild type GG or single mutant GA.

The significance analysis results show that, the genotype of Scaffold451: 940283 is extremely significantly correlated with (+)-catechin content, the correlation coefficient is 0.54, p-value is $8.76 \times 10^{-16}$, F-value (6.91/3.94) is 92.9, which is a recessive mutation, the (+)-catechin content in the dry matter of tea soup corresponding to a TT genotype sample has extremely significant difference compared with CC and CT genotype samples. It is statistically judged that, when the genotype of the sample is double mutant TT, the (+)-catechin content in the dry matter in the tea plant is more likely to be higher than the normal average of the sample of which the genotype is wild type CC or single mutant CT.

The significance analysis results show that, the genotype of Scaffold3727:442660 is extremely significantly correlated with (+)-catechin content, the correlation coefficient is 0.64, p-value is $1.60 \times 10^{-12}$, F-value (6.91/3.94) is 65.9, which is a recessive mutation, the (+)-catechin content in the dry matter of tea soup corresponding to an AA genotype sample has extremely significant difference compared with GG and GA genotype samples. It is statistically judged that, when the genotype of the sample is double mutant AA, the (+)-catechin content in the dry matter in the tea plant is more likely to be higher than the normal average of the sample of which the genotype is wild type GG or single mutant GA.

The significance analysis results show that, the genotype of Scaffold115: 803980 is extremely significantly correlated with (+)-catechin content, the correlation coefficient is 0.70, p-value is $8.79 \times 10^{-16}$, F-value (6.91/3.94) is 92.95, which is a recessive mutation, the (+)-catechin content in the dry matter of the tea plant corresponding to a GG genotype sample has extremely significant difference compared with AA and GA genotype samples, it is statistically judged that, when the genotype of the sample is double mutant GG, the (+)-catechin content in the dry matter in the tea plant is more likely to be higher than the sample of which the genotype is wild type AA or single mutant GA.

The significance analysis results show that, the genotype of Scaffold920: 281727 is extremely significantly correlated with (+)-catechin content, the correlation coefficient is 0.54, p-value is $1.19 \times 10^{-8}$, F-value (6.91/3.94) is 38.92, which is a recessive mutation, the (+)-catechin content in the dry matter of the tea plant corresponding to a GG genotype sample has extremely significant difference compared with AA and GA genotype samples, it is statistically judged that, when the genotype of the sample is double mutant GG, the (+)-catechin content in the dry matter in the tea plant is more likely to be higher than the sample of which the genotype is wild type AA or single mutant GA.

Embodiment 3 Kit for Evaluating Tea Plant (+)-Catechin Content

I. Composition

The primers for the SNP site 1 which have the nucleotide sequences shown as SEQ ID NO: 2 and SEQ ID NO: 3, the primers for the SNP site 2 which have the nucleotide sequences shown as SEQ ID NO: 5 and SEQ ID NO: 6, the primers for the SNP site 3 which have the nucleotide sequences shown as SEQ ID NO: 8 and SEQ ID NO: 9, the primers for the SNP site 4 which have the nucleotide sequences shown as SEQ ID NO: 11 and SEQ ID NO: 12, the primers for the SNP site 5 which have the nucleotide sequences shown as SEQ ID NO: 14 and SEQ ID NO: 15, the primers for the SNP site 6 which have the nucleotide sequences shown as SEQ ID NO: 17 and SEQ ID NO: 18, the primers for the SNP site 7 which have the nucleotide sequences shown as SEQ ID NO: 20 and SEQ ID NO: 21, and/or the primers for the SNP site 8 which have the nucleotide sequences shown as SEQ ID NO: 23 and SEQ ID NO: 24, 2×Taq PCR Master Mix, ddH$_2$O.

In particular, primer F for SNP site 1: GAAGACTAACCCGTATCGAG (SEQ ID NO: 2);
  primer R for SNP site 1: ACACTTACAGTCTCTTGCGG (SEQ ID NO: 3);
  primer F for SNP site 2: GATGACACAACCCTCATCTG (SEQ ID NO: 5);
  primer R for SNP site 2: AATGTATGCCCGGTAAGGAC (SEQ ID NO: 6);
  primer F for SNP site 3: TCTCTGCACTGTTGTCACTC (SEQ ID NO: 8);
  primer R for SNP site 3: CACCACACTTTCTTAGAAGG (SEQ ID NO: 9);
  primer F for SNP site 4: GATTTGACCTTCAACGTGGG (SEQ ID NO: 11);
  primer R for SNP site 4: TGCAGCGTTTGTGTTTGCAG (SEQ ID NO: 12);
  primer F for SNP site 5: GTAATAGACGGTGCAAACCC (SEQ ID NO: 14);
  primer R for SNP site 5: CAAAGTATTTGGGAGCGCTG (SEQ ID NO: 15);
  primer F for SNP site 6: TTGTCCGTGTCCAATCCTTG (SEQ ID NO: 17);
  primer R for SNP site 6: ATTGACCACCTGGAAGAAGC (SEQ ID NO: 18);
  primer F for SNP site 7: CTTCATCTCCACCACACTTC (SEQ ID NO: 20);
  primer R for SNP site 7: GCCCAAAGTAGCAAAGAGAG (SEQ ID NO: 21);
  primer F for SNP site 8: TTCGCATTCGTCCTTTTGGG (SEQ ID NO: 23);
  primer R for SNP site 8: ACGTGCTACATTCTCCATCC (SEQ ID NO: 24).

II. Usage Method (1) The CTAB method was used to extract total DNA from buds of tea plant, it was ensured that A260/A280 of each DNA sample was between 1.8 and 2.0, and the concentration was greater than 100 μg/μl;

(2) PCR Amplification

Detection primers with nucleotide sequences shown as SEQ ID NO: 2 and SEQ ID NO: 3, SEQ ID NO: 5 and SEQ ID NO: 6, SEQ ID NO: 8 and SEQ ID NO: 9, SEQ ID NO: 11 and SEQ ID NO: 12, SEQ ID NO: 14 and SEQ ID NO: 15, SEQ ID NO: 17 and SEQ ID NO: 18, SEQ ID NO: 20 and SEQ ID NO: 21, and SEQ ID NO: 23 and SEQ ID NO: 24 were used for detecting SNP site 1, SNP site 2, SNP site 3, SNP site 4, SNP site 5, SNP site 6, SNP site 7 and SNP site 8, respectively.

| 2 × Taq PCR Master Mix | 5 μl |
| --- | --- |
| primers | Each 0.5 μl |
| DNA template | 1 μl |
| ddH$_2$O | 3 μl |

PCR amplification procedure was as follows:

| 95° C. | 5 minutes | |
| --- | --- | --- |
| 95° C. | 30 seconds | ×45 cycles |
| 56° C. | 30 seconds | |
| 72° C. | 30 seconds | |
| 72° C. | 2 minutes | |
| 4° C. | forever | |

(3) Product Purification

The PCR amplification products were subjected to gel electrophoresis, followed by recovery and purification using a commercially available gel electrophoresis DNA recovery kit.

A band with a fragment length of about 240 bp in the amplification product of the primers shown in SEQ ID NO: 2 and SEQ ID NO: 3 was selected for recovery and purification.

A band with a fragment length of about 240 bp in the amplification product of the primers shown in SEQ ID NO: 5 and SEQ ID NO: 6 was selected for recovery and purification.

A band with a fragment length of about 240 bp in the amplification product of the primers shown in SEQ ID NO: 8 and SEQ ID NO: 9 was selected for recovery and purification.

A band with a fragment length of about 240 bp in the amplification product of the primers shown in SEQ ID NO: 11 and SEQ ID NO: 12 was selected for recovery and purification.

A band with a fragment length of about 240 bp in the amplification product of the primers shown in SEQ ID NO: 14 and SEQ ID NO: 15 was selected for recovery and purification.

A band with a fragment length of about 240 bp in the amplification product of the primers shown in SEQ ID NO: 17 and SEQ ID NO: 18 was selected for recovery and purification.

A band with a fragment length of about 240 bp in the amplification product of the primers shown in SEQ ID NO: 20 and SEQ ID NO: 21 was selected for recovery and purification.

A band with a fragment length of about 240 bp in the amplification product of the primers shown in SEQ ID NO: 23 and SEQ ID NO: 24 was selected for recovery and purification.

(4) Sequencing and Interpretation of Results

The amplification products of the primers shown in SEQ ID NO: 2 and SEQ ID NO: 3 were recovered and purified and sent to a sequencing company for Sanger sequencing.

The sequencing results were compared with the nucleotide sequence shown in SEQ ID NO: 1. According to FIG. 2 (bold and underlined parts denote upstream and downstream primers), the site Scaffold4239:309117 is located at the 73rd base of the amplification product. It is statistically judged that, when the genotype of the sample is double mutant AA, the (+)-catechin content in the dry matter in the tea plant is more likely to be higher than the normal average of the sample of which the genotype is wild type GG or single mutant GA.

The amplification products of the primers shown in SEQ ID NO: 5 and SEQ ID NO: 6 were recovered and purified and sent to a sequencing company for Sanger sequencing. The sequencing results were compared with the nucleotide sequence shown in SEQ ID NO: 4. According to FIG. 3 (bold and underlined parts denote upstream and downstream primers), the site Scaffold3614: 66549 is located at the 137th base of the amplification product. It is statistically judged that, when the genotype of the sample is double mutant CC, the (+)-catechin content in the dry matter in the tea plant is more likely to be higher than the sample of which the genotype is wild type TT or single mutant CT.

The amplification products of the primers shown in SEQ ID NO: 8 and SEQ ID NO: 9 were recovered and purified and sent to a sequencing company for Sanger sequencing. The sequencing results were compared with the nucleotide sequence shown in SEQ ID NO: 7. According to FIG. 4 (bold and underlined parts denote upstream and downstream primers), the site Scaffold349: 3413816 is located at the 160th base of the amplification product. It is statistically judged that, when the genotype of the sample is double mutant GG, the (+)-catechin content in the dry matter in the tea plant is more likely to be higher than the sample of which the genotype is wild type AA or single mutant GA.

The amplification products of the primers shown in SEQ ID NO: 11 and SEQ ID NO: 12 were recovered and purified and sent to a sequencing company for Sanger sequencing. The sequencing results were compared with the nucleotide sequence shown in SEQ ID NO: 10. According to FIG. 5 (bold and underlined parts denote upstream and downstream primers), the site Scaffold1989: 2316385 is located at the 175th base of the amplification product. It is statistically judged that, when the genotype of the sample is double mutant AA, the (+)-catechin content in the dry matter in the tea plant is more likely to be higher than the normal average of the sample of which the genotype is wild type GG or single mutant GA.

The amplification products of the primers shown in SEQ ID NO: 14 and SEQ ID NO: 15 were recovered and purified and sent to a sequencing company for Sanger sequencing. The sequencing results were compared with the nucleotide sequence shown in SEQ ID NO: 13. According to FIG. 6 (bold and underlined parts denote upstream and downstream primers), the site Scaffold451: 940283 is located at the 161st base of the amplification product. It is statistically judged that, when the genotype of the sample is double mutant TT, the (+)-catechin content in the dry matter in the tea plant is more likely to be higher than the normal average of the sample of which the genotype is wild type CC or single mutant CT.

The amplification products of the primers shown in SEQ ID NO: 17 and SEQ ID NO: 18 were recovered and purified and sent to a sequencing company for Sanger sequencing. The sequencing results were compared with the nucleotide sequence shown in SEQ ID NO: 16. According to FIG. 7 (bold and underlined parts denote upstream and downstream primers), the site Scaffold3727:442660 is located at the 197th base of the amplification product. It is statistically judged that, when the genotype of the sample is double mutant AA, the (+)-catechin content in the dry matter in the tea plant is more likely to be higher than the normal average of the sample of which the genotype is wild type GG or single mutant GA.

The amplification products of the primers shown in SEQ ID NO: 20 and SEQ ID NO: 21 were recovered and purified and sent to a sequencing company for Sanger sequencing. The sequencing results were compared with the nucleotide sequence shown in SEQ ID NO: 19. According to FIG. 8 (bold and underlined parts denote upstream and downstream primers), the site Scaffold115: 803980 is located at the 164th base of the amplification product. It is statistically judged that, when the genotype of the sample is double mutant GG, the (+)-catechin content in the dry matter in the tea plant is more likely to be higher than the sample of which the genotype is wild type AA or single mutant GA.

The amplification products of the primers shown in SEQ ID NO: 23 and SEQ ID NO: 24 were recovered and purified and sent to a sequencing company for Sanger sequencing. The sequencing results were compared with the nucleotide sequence shown in SEQ ID NO: 22. According to FIG. 9 (bold and underlined parts denote upstream and downstream primers), the site Scaffold920: 281727 is located at the 106th base of the amplification product. It is statistically judged that, when the genotype of the sample is double mutant GG, the (+)-catechin content in the dry matter in the tea plant is more likely to be higher than the sample of which the genotype is wild type AA or single mutant GA.

Embodiment 4 Use of Kit for Evaluating Tea Plant (+)-Catechin Content

I. Experimental Method

The kit in Embodiment 3 was used to detect 98 tea plant samples in Embodiment 2.

II. Experiment Results

The detection results are consistent with those of Embodiment 2 using the SnapShot technology platform. This kit can be used to evaluate the tea plant (+)-catechin content. The sequencing peaks of some samples are shown in FIG. 34 to FIG. 38.

What is claimed is:

1. A method for evaluating tea plant (+)-catechin content, comprising detecting a genotype of a molecular marker by using a pair of primers of the molecular marker for detecting and evaluating the tea plant (+)-catechin content, wherein the primers consist of nucleotide sequences shown as SEQ ID NO:17 and SEQ ID NO:18, and the molecular marker is located at a SNP site of tea genomes Scaffold3727:442660, which is the 501st base of SEQ ID NO:16, when the genotype of a sample is double mutant AA, the (+)-catechin content in a dry matter in the tea plant is higher than that of a normal average of the sample of which the genotype is a wild type GG or a single mutant GA.

* * * * *

SEQUENCE LISTING

```
Sequence total quantity: 45
SEQ ID NO: 1           moltype = DNA  length = 1001
FEATURE                Location/Qualifiers
source                 1..1001
                       mol_type = genomic DNA
                       organism = Camellia sinensis
SEQUENCE: 1
```

```
gaaggctctg gagtagctga agttgttatg agcttgtcta ggccgaaatc agcgaggtga    60
gcttcaaaat cggcgtcgaa taggacgttc tgaggcttga catcgccatg aaccatggcg   120
gtggagtgga ggaaggcgag gccgcgggcg attccgaggg ctattaggtg gcgcattggc   180
caattcaata catgcccgtc ttggtgagaa gcttcttgaa gcaatgtggc taggtttccg   240
ttaggcatat agtcgtagac taagagtctg aggtctgtga gtccggcgaa gtacccacgg   300
aggactgtga ggtttctgtg cttcactctc ccgagcgatt cggcttcttt tctgaacatg   360
ttttcgtcta gcgatccatc agggagtctc cgaatcgaaa gcaccattcc atcactgtaa   420
caggctttga agactaaccc gtatcgagtc ctgcttagaa cgttctcttc atcgaattgt   480
ctcgttgctt cggttgtttc ngctagagtg atcttgttat tgaacataac aagctttgga   540
ccgccattat cgccacttcc acgacctccg ctggctgcag ctgagcttgc tcttgctggg   600
ctgcgctttt tctctccggc agccttttct ttgagcctct tgcgccaccg caagagactg   660
taagtgtaga agcaacaaca cagtgctaag aggaaaccac cactaacagc catggcaata   720
aacatgatca gcctcttctt cctattactc atctcttcgc atttcgtgct taagggtttc   780
ccacataagt tcggatttcc tgcataatca gatggatcgt tgaatcttga agccagcatt   840
gttggaatct cgccggagag gttgttttgg gatacattga agtagaccaa gctagagatg   900
agtgaaatgt ttgctggaat cggtccggtc aggttgtttg cagagagatt gaggactgtg   960
aggtttgata aattggacaa tgagtctggt atttggcctg g                      1001

SEQ ID NO: 2               moltype = DNA   length = 20
FEATURE                    Location/Qualifiers
source                     1..20
                           mol_type = other DNA
                           organism = Camellia sinensis
SEQUENCE: 2
gaagactaac ccgtatcgag                                                20

SEQ ID NO: 3               moltype = DNA   length = 20
FEATURE                    Location/Qualifiers
source                     1..20
                           mol_type = other DNA
                           organism = Camellia sinensis
SEQUENCE: 3
acacttacag tctcttgcgg                                                20

SEQ ID NO: 4               moltype = DNA   length = 1001
FEATURE                    Location/Qualifiers
source                     1..1001
                           mol_type = genomic DNA
                           organism = Camellia sinensis
SEQUENCE: 4
gagtcatggg tttcttaaat ttctctaaaa aatatttagg tggtgactct gtatctggca    60
aaatagtcca ttttttggcaa tttgattcaa aatcagtttt ccaacatatt tgccgaattg   120
ggacttttg gtgattatct atttcacatt gcacatgtga aatcagattc agaaccgtgg   180
gagtccgata ctgctagggct tattcgtctt ccgaaaaggg gcatgcaaag tcgaactaca   240
agtcccctgg ggaggatgga ttgcaaaatt accgtacaca gtagcaatcc cgtctttaaa   300
ggcgtacttt accaactgat ggaccattga tgacacaacc ctcatctgat gtagccaggg   360
tcttcccagt agtagattga aagtgtccga aacatccgat acatagaatt taacctgatg   420
ctcagacggg ccgagtagga tatggctctt aaacattacc atgacatctt ggctcgtatt   480
gtcatataag cctaaacggc ntgggtcgtg ggcgtaaagt tagtcggcct cacaccgatg   540
gcataggcgg tccttaccgg gcatacatta atcgccgatc cgttatctac caacaccact   600
ggaatccact ttttctgact ttccagcgtt acatataagg gccaattgtg ttagcaccc   660
tcaggtggta actctttatc tataaaagat atcactggcg taacatcccc ggatgtaacc   720
aatgatacca attggtcagc agtggtttcg ataggggagtt tggtccggtt cattgcctct   780
agcagcagtg cctgtctatg ctcccgagat gccatgatta gccccagat tgatatgtcg   840
gcctgaatct tcttaagctg tttcaagacc aggttttcct ctcttttgat   900
ttctcgaccc ccactgtcct tgatatatgc catcttttag ggttatcacc cattggtacc   960
cctttcggtc tagattaccc tgactttaag gtctccttct c                      1001

SEQ ID NO: 5               moltype = DNA   length = 20
FEATURE                    Location/Qualifiers
source                     1..20
                           mol_type = other DNA
                           organism = Camellia sinensis
SEQUENCE: 5
cttcatctcc accacacttc                                                20

SEQ ID NO: 6               moltype = DNA   length = 20
FEATURE                    Location/Qualifiers
source                     1..20
                           mol_type = other DNA
                           organism = Camellia sinensis
SEQUENCE: 6
aatgtatgcc cggtaaggac                                                20

SEQ ID NO: 7               moltype = DNA   length = 1001
FEATURE                    Location/Qualifiers
source                     1..1001
                           mol_type = genomic DNA
                           organism = Camellia sinensis
```

```
SEQUENCE: 7
ataatctttt tgtacttgtt caggtggaat gaagcaatca accgagagtc caggaacatt    60
gaatgctagg tcgtcgatct tccaagtctc ctccatccgt gtgattgctg tgcccgctct   120
cagattgtcc ccaaatcttg agatgatcac acttgattgg ccagaatgcg cgatcatcgt   180
gccctccacc atccgatagt cctcgatttt cgtgcccatg gtggtctccc aataggtagg   240
gtaggttccg ggggactgga ttctggtgag gtaagagtcc tctaaataca ctagcagacc   300
acttctttgg ctgaagtaac caaacatgac atgcttgatc atctctgcac tgttgtcact   360
ccgatcggct aggtccgtct gatccgcgga caatttcaac acgaagcaat cgacgctcaa   420
gattcgtttt tcgcccacgt attgtgctag ggaaaacaca gccgatacag ccacaggatc   480
tagtccctgc ataaataaca ntatgttttt tacatagagg aaaataatat ctgtcacatg   540
aattctactc catttttttaa ccttctaaga aagtgtggtg aaaaaaatat taaatccatt   600
gggtaaaata taacagtctt taacataaca atatggcgaa ctatacattc aattctagaa   660
aatgtctcat ttttatagat ttttatgaaa gggatcaacc ttcttttttt ttattggaag   720
cactatataa ataatgtcaa atagttttcc aaacttatct aaataaagtt ttaataattt   780
taatccacac attttgaatt taatttactt atttttagta gataacatta ccacagtcaa   840
aaagagtgcc aacatgaacc tccagcacac ttgaagagca cttgacgatc atattgggaa   900
agttaccagc cagcactccc aaaaaaaaaa aagaaaaaa agataaaaga ttaaaaaaat   960
tagtaaaaag tgactttaca aaaaggaata ttccacctct g                      1001

SEQ ID NO: 8              moltype = DNA   length = 20
FEATURE                   Location/Qualifiers
source                    1..20
                          mol_type = other DNA
                          organism = Camellia sinensis
SEQUENCE: 8
tctctgcact gttgtcactc                                                20

SEQ ID NO: 9              moltype = DNA   length = 20
FEATURE                   Location/Qualifiers
source                    1..20
                          mol_type = other DNA
                          organism = Camellia sinensis
SEQUENCE: 9
caccacactt tcttagaagg                                                20

SEQ ID NO: 10             moltype = DNA   length = 1001
FEATURE                   Location/Qualifiers
source                    1..1001
                          mol_type = genomic DNA
                          organism = Camellia sinensis
SEQUENCE: 10
aattaataaa gacttgaaca gtgaggagga caatggagag agggatttca tggaggagtt    60
tcagagaatt agcttatttg atgagttgtt tattttatt tatttttattt ttacttacag   120
tggtagatgc atcccatccc catcatcgtc ccaatcgtta ttgccatgat tttcatgttt   180
catcaggtgt tgcttctctt gtttgtgctt ccaactttcc atcctctctt tccaagctac   240
gctgccatag ccataagcag ccaaatcctt ggaaggatcc atggatcgag attgcactgc   300
aaaaatgggc aggggattat catacagatt tgaccttcaa cgtgggaggg aggggagata   360
aaaggaaacc atagcgtagc gtagcatagc ataggaaagc aaagcagaat taattaaaat   420
taccgggtag gctaggatct gagaaaggaa gtggatgaat ccttctgctg ctgctgctgc   480
tgccaccacc aacacccact ntcgatgaaa ccaatgcatg ttgttcagga ggaatatcat   540
catccacctg caaacacaaa cgctgcaggt ctcaggctcc tgctgtctga aatttgcata   600
caatgatttt tagaattcca cagcaacagc aacagcaaca gcaacggtag tcgtaccata   660
tggccgttgg taaggagggg aagttgaggc aaagtattac tattattagt attgtgaaag   720
acatgtgggt gcaattcgga tgagtcgaaa atatggccat agctcatgtg cgaaccaccg   780
tgaccgtgaa gtatagcctc tgaacgagca agagagtgct gctgtgaatc cagtagttta   840
gcactgtcac gaaccctccc ttcaaaattg aactcgttttt ccacatcgtc aatgtcatct   900
tcttcttcat caccctccac tctagcacac cctgcatcat tcatccatcc attgatcatc   960
cgggtagaac taacaaattt taacaaatat cgaatccccc c                      1001

SEQ ID NO: 11             moltype = DNA   length = 20
FEATURE                   Location/Qualifiers
source                    1..20
                          mol_type = other DNA
                          organism = Camellia sinensis
SEQUENCE: 11
gatttgacct tcaacgtggg                                                20

SEQ ID NO: 12             moltype = DNA   length = 20
FEATURE                   Location/Qualifiers
source                    1..20
                          mol_type = other DNA
                          organism = Camellia sinensis
SEQUENCE: 12
tgcagcgttt gtgtttgcag                                                20

SEQ ID NO: 13             moltype = DNA   length = 1001
FEATURE                   Location/Qualifiers
source                    1..1001
                          mol_type = genomic DNA
```

```
                         organism = Camellia sinensis
SEQUENCE: 13
cggcgggctg ttccaagaaa aaatataaaa ttaaataagt ttgtatattg tcctgccggg      60
aaacaaatgt ggaatcatta caaagaatta agagaagcac ttacattgct ccatcttttta    120
tcgagaaatt cattgatcgc aatggcgttt tgtccgtaca tcataggagt cggaagagtg    180
agagagccat ctgatgcaca ctaaagaagg acagaaactg tttgaggaac ctgaacattt    240
tgaggataag tcaaaaaaag ttaattaggt ttcggagtcc agtgattgtc gaaccaacaa    300
aacaaaactt atatgctgta aaagaacttc aacttaccta gtaatagacg gtgcaaaccc    360
aattgtatag taggtaagta cgatccatat cacagattcc atgaatgaaa cggaattcc    420
gaggagccaa attggcaagc taaaagccca tgcaggaaaa acaagctat ccctctgttt    480
aaagaacacg ggaagcttac naaccgtcat tgcaagctct gccatcccat tgaacattat    540
attaacaaga ctgaaaaaca cgctcccaa atactttgaa gcatcttcta ctgttccggt    600
tttcatttct gttcttaaaa aaacagtgag ggcaattgtg gccatgattg ttatctgagt    660
ggttttgaat atgtatgtga aagagttgcg cttcattage agccactccc tcgataagca    720
tgccttgaag agttcccgat tggagatgcc ataactctca gtcaccaacg cagcagggtg    780
ggctttggac tggtcataag gaattctaag ttcttcagtc atctgttgcc cgatgtggaa    840
agagttgaag gcctgtgcaa agtcgttcac cgagacatat ctgtaaggtt ggttcttttt    900
gaaccaatac tgttcttggt ccttcttgga agttactact tggagaaaat ctgcaactcc    960
tttcctttg gggcatttga atcccatata ttcaaagaac t                        1001

SEQ ID NO: 14            moltype = DNA   length = 20
FEATURE                  Location/Qualifiers
source                   1..20
                         mol_type = other DNA
                         organism = Camellia sinensis
SEQUENCE: 14
gtaatagacg gtgcaaaccc                                                 20

SEQ ID NO: 15            moltype = DNA   length = 20
FEATURE                  Location/Qualifiers
source                   1..20
                         mol_type = other DNA
                         organism = Camellia sinensis
SEQUENCE: 15
caaagtattt gggagcgctg                                                 20

SEQ ID NO: 16            moltype = DNA   length = 1001
FEATURE                  Location/Qualifiers
source                   1..1001
                         mol_type = genomic DNA
                         organism = Camellia sinensis
SEQUENCE: 16
ccctacactt tttttttaaa tggtgagttg tccccacact tcaatatcgc acataataca    60
cgttttcatt tcatgtcgtc ttcaatacag aagactcgca ccactattag ctagcctatt    120
atagcccctc ctcttaacta cctctacccc caattcctct ctctctctct ctctctctct    180
ctctctctct ctctctataa aatcaaaaat aaggacttgt ttgtttcatc gtactttgtt    240
ttataggatc aaccttggaa gccacaccta ggcatgagtt gtcaataga ttggccagaa    300
ccaattgtcc gtgtccaatc cttgtccgac agcggcaccc ccaccatccc cgactgctac    360
gtcaaaccgc cacaggaccg gccggtagtc aactcctcct ccaaccacca tgacaccgat    420
gtaaacatcc ccttaattga cctcggagtt ttaacatccg gggacgacaa tactactcta    480
agagcaacca ccatagccca natatccgaa gcgtgtcgtg agtggggctt cttccaggtg    540
gtcaatcacg gagtgagccc ccacttgatg gatcgcgcca gggatatctg gcgcgatttc    600
ttccatcttc caatgaaga aaagcaagtt tatgcgaatt cacccaaaac gtacgaaggg    660
tatgcaagtc ggttaggcgt ccagaaaggt gccattctcg actggagcga ctactacttc    720
ttgcactttc ttccgtgctc gcttaaagat cataacaagt ggcccgcctt gccagctcct    780
ctcaggtgaa ttgctttaat ttttaatttt ttaatgtaat aataatatat aaatgttggt    840
gacttgtata ctttaatgta acaaccacca tctatttgga ctttactgat ctaatttat    900
gtattactat attactggtt gtgtttaggg aagtgataga tgagtacgcg gaccacttag    960
taaagctaag tgggcgatta atgaaggttt tgtcaataaa t                        1001

SEQ ID NO: 17            moltype = DNA   length = 20
FEATURE                  Location/Qualifiers
source                   1..20
                         mol_type = other DNA
                         organism = Camellia sinensis
SEQUENCE: 17
ttgtccgtgt ccaatccttg                                                 20

SEQ ID NO: 18            moltype = DNA   length = 20
FEATURE                  Location/Qualifiers
source                   1..20
                         mol_type = other DNA
                         organism = Camellia sinensis
SEQUENCE: 18
attgaccacc tggaagaagc                                                 20

SEQ ID NO: 19            moltype = DNA   length = 1001
FEATURE                  Location/Qualifiers
source                   1..1001
```

```
                         mol_type = genomic DNA
                         organism = Camellia sinensis
SEQUENCE: 19
aatcattaag agtcattatg gtaatcatga gcttaattac tccaagtaaa gccaatcttc    60
atcatagaaa taaaaattac aaaaaaaaaa aaaaaaaaaa agtctttcag ctgaacaacc   120
catccctgca actgcaccac cataattgag atctaaatct gaaggaactt gcttgagatc   180
taaatctgaa ggaacttgct tgcttaggaa catccacatc catgatttct acaattttttg  240
gaagacacag aaccagagaa gatgactcaa aatcaagcag caattgtaag aaaattcgac   300
caatcgaaat catcttggaa ttaatcattg tagcctcctt catctccacc acacttctcc   360
tcctacttcc atgcgattac gtcgacggca gccctattcc caccatcata ttcaaaggac   420
tcccctccac cttccacgcc ttcgtcgtct ccctcatctt cgccttctcc ggagccttga   480
gcgccttgtt gatccacgac ncatccctct ttgccaagct ctgcgagttc tcttccatgg   540
cctccatgac ctctgctctc tctttgctac tttgggctat gttcttcacc tgttttcaac   600
cacaacccag gtaaaactcg aattcagaca tcacatggta agaaaacaag ttattaaggt   660
ttttaacctt ataaagactt ttttttcttt tctttttcct tcctgtccaa cggacacgtg   720
gtgtgtttta aaattaataa atcgtgtatc agatatggat atacaatcgc gtggtcagtt   780
gaaattacta ttggtatgct ttatataccg tgtcgtgtgt aaaattaaaa cttgttttgt   840
gatgttgttg gtctgttatg tacttggtgt tgttgaaata atattaccat aaatttgaat   900
aagcctttat tatgtggaga tccgatggat taatgatgca tatttgtcaca gaattcaaaa   960
tgatttcatt ttgagcatgg tgacgagggt tccaagccct g                      1001

SEQ ID NO: 20            moltype = DNA  length = 20
FEATURE                  Location/Qualifiers
source                   1..20
                         mol_type = other DNA
                         organism = Camellia sinensis
SEQUENCE: 20
cttcatctcc accacacttc                                                20

SEQ ID NO: 21            moltype = DNA  length = 20
FEATURE                  Location/Qualifiers
source                   1..20
                         mol_type = other DNA
                         organism = Camellia sinensis
SEQUENCE: 21
gcccaaagta gcaaagagag                                                20

SEQ ID NO: 22            moltype = DNA  length = 1001
FEATURE                  Location/Qualifiers
source                   1..1001
                         mol_type = genomic DNA
                         organism = Camellia sinensis
SEQUENCE: 22
agggagactt ttatcttgag agctagaaga agagaaagtt agagaaaaga aagagaagta    60
ggaagaaaat caaagggaat tcacattcgt ccttttggag ttgagaattg aacacttagg   120
tgatttcgaa aatcataaat gaggtgtgtt aaactaatat cgttcagcta cagttactca   180
gtaaattctc tttctcagag gctacgcagg tgtagtttga gttaaacttg gccacttaaa   240
ctaatggaac cattagggc ccaagctaat tagttcctag aacaaaggag agaggacgga   300
gaagcataga gaaagttaga gagaaacttt tttcttgaga gatagaagag atagttagag   360
aaaagaaaga gaaacgggaa aaaaatcatt gggaattcgc attcgtccctt ttgggcttga   420
gaattgaaca gttggggaat ttgggaaacc ttaaatgcgg tgcttatgtt taactaatat   480
cgttaagtgc caattactca ntaaatcctc tttcttagat gctaagcaag atttagtgta   540
gttaaacttg gccacttaag ctaatggaac agttagggtc ccaagcgaat tagtttccta   600
gaacaaaaga tagaaggatg gagaatgtag cacgttcgtg agggaccccg ctactacagt   660
tcggactcga tttgtgtcac ggttcttaat ctgaaccaaa gagtccaaat ccggcaaatc   720
gttttgagaa acagatttttt tgaaaagaag tgccaaacat ggactgcttt gctagatata   780
gagtcgccac ctaaatattt ttttaaaatg gggaaattta ggaaacccta acttggtgcc   840
aaaggccacg tgtccgtcat tgccaaagtt gcctgggctc gggagcttgg gtacgattgg   900
ggaaggtcag ctatgagcac cccctctcgc ccgatccgaa gatcggcctc tactaaccgt   960
gatatccgtt tttgaaaacg ttatgtgttc ttaaaccaat t                      1001

SEQ ID NO: 23            moltype = DNA  length = 20
FEATURE                  Location/Qualifiers
source                   1..20
                         mol_type = other DNA
                         organism = Camellia sinensis
SEQUENCE: 23
ttcgcattcg tccttttggg                                                20

SEQ ID NO: 24            moltype = DNA  length = 20
FEATURE                  Location/Qualifiers
source                   1..20
                         mol_type = other DNA
                         organism = Camellia sinensis
SEQUENCE: 24
acgtgctaca ttctccatcc                                                20

SEQ ID NO: 25            moltype = DNA  length = 20
FEATURE                  Location/Qualifiers
```

```
source                      1..20
                            mol_type = other DNA
                            organism = Camellia sinensis
SEQUENCE: 25
ccgcaagaga ctgtaagtgt                                                   20

SEQ ID NO: 26               moltype = DNA   length = 20
FEATURE                     Location/Qualifiers
source                      1..20
                            mol_type = other DNA
                            organism = Camellia sinensis
SEQUENCE: 26
gtccttaccg ggcatacatt                                                   20

SEQ ID NO: 27               moltype = DNA   length = 20
FEATURE                     Location/Qualifiers
source                      1..20
                            mol_type = other DNA
                            organism = Camellia sinensis
SEQUENCE: 27
ccttctaaga aagtgtggtg                                                   20

SEQ ID NO: 28               moltype = DNA   length = 20
FEATURE                     Location/Qualifiers
source                      1..20
                            mol_type = other DNA
                            organism = Camellia sinensis
SEQUENCE: 28
ctgcaaacac aaacgctgca                                                   20

SEQ ID NO: 29               moltype = DNA   length = 20
FEATURE                     Location/Qualifiers
source                      1..20
                            mol_type = other DNA
                            organism = Camellia sinensis
SEQUENCE: 29
cagcgctccc aaatactttg                                                   20

SEQ ID NO: 30               moltype = DNA   length = 20
FEATURE                     Location/Qualifiers
source                      1..20
                            mol_type = other DNA
                            organism = Camellia sinensis
SEQUENCE: 30
gcttcttcca ggtggtcaat                                                   20

SEQ ID NO: 31               moltype = DNA   length = 20
FEATURE                     Location/Qualifiers
source                      1..20
                            mol_type = other DNA
                            organism = Camellia sinensis
SEQUENCE: 31
ctctctttgc tactttgggc                                                   20

SEQ ID NO: 32               moltype = DNA   length = 20
FEATURE                     Location/Qualifiers
source                      1..20
                            mol_type = other DNA
                            organism = Camellia sinensis
SEQUENCE: 32
ggatggagaa tgtagcacgt                                                   20

SEQ ID NO: 33               moltype = DNA   length = 47
FEATURE                     Location/Qualifiers
source                      1..47
                            mol_type = other DNA
                            organism = Camellia sinensis
SEQUENCE: 33
ctgactgact gactgactga ctattgtctc gttgcttcgg ttgtttc                     47

SEQ ID NO: 34               moltype = DNA   length = 27
FEATURE                     Location/Qualifiers
source                      1..27
                            mol_type = other DNA
                            organism = Camellia sinensis
SEQUENCE: 34
gactactaac tttacgccca cgaccca                                           27

SEQ ID NO: 35               moltype = DNA   length = 38
```

```
FEATURE               Location/Qualifiers
source                1..38
                      mol_type = other DNA
                      organism = Camellia sinensis
SEQUENCE: 35
actgactgac taaggatcta gtccctgcat aaataaca                          38

SEQ ID NO: 36         moltype = DNA   length = 24
FEATURE               Location/Qualifiers
source                1..24
                      mol_type = other DNA
                      organism = Camellia sinensis
SEQUENCE: 36
ctgctgccac caccaacacc cact                                         24

SEQ ID NO: 37         moltype = DNA   length = 31
FEATURE               Location/Qualifiers
source                1..31
                      mol_type = other DNA
                      organism = Camellia sinensis
SEQUENCE: 37
actgactgtt taaagaacac gggaagctta c                                 31

SEQ ID NO: 38         moltype = DNA   length = 28
FEATURE               Location/Qualifiers
source                1..28
                      mol_type = other DNA
                      organism = Camellia sinensis
SEQUENCE: 38
ataatctaag agcaaccacc atagccca                                     28

SEQ ID NO: 39         moltype = DNA   length = 49
FEATURE               Location/Qualifiers
source                1..49
                      mol_type = other DNA
                      organism = Camellia sinensis
SEQUENCE: 39
gactgactga ctgactgact gactcagcag agcttggcaa agagggatg              49

SEQ ID NO: 40         moltype = DNA   length = 56
FEATURE               Location/Qualifiers
source                1..56
                      mol_type = other DNA
                      organism = Camellia sinensis
SEQUENCE: 40
tgactgactg actgactgac tgactgactg acttagcatc taagaaagag gattta      56

SEQ ID NO: 41         moltype = DNA   length = 21
FEATURE               Location/Qualifiers
source                1..21
                      mol_type = other DNA
                      organism = Camellia sinensis
SEQUENCE: 41
tcactctagc tgaaacaacc g                                            21

SEQ ID NO: 42         moltype = DNA   length = 21
FEATURE               Location/Qualifiers
source                1..21
                      mol_type = other DNA
                      organism = Camellia sinensis
SEQUENCE: 42
aacacccact gtcgatggaa c                                            21

SEQ ID NO: 43         moltype = DNA   length = 21
FEATURE               Location/Qualifiers
source                1..21
                      mol_type = other DNA
                      organism = Camellia sinensis
SEQUENCE: 43
ataaataaca atatgttttt t                                            21

SEQ ID NO: 44         moltype = DNA   length = 21
FEATURE               Location/Qualifiers
source                1..21
                      mol_type = other DNA
                      organism = Camellia sinensis
SEQUENCE: 44
gatccacgac acatccctct t                                            21
```

| | |
|---|---|
| SEQ ID NO: 45 | moltype = DNA   length = 21 |
| FEATURE | Location/Qualifiers |
| source | 1..21 |
| | mol_type = other DNA |
| | organism = Camellia sinensis |
| SEQUENCE: 45 | |
| agaggattta ttgagtaatt g | 21 |